(12) United States Patent
Takahashi et al.

(10) Patent No.: US 10,053,570 B2
(45) Date of Patent: Aug. 21, 2018

(54) ANTIVIRAL VINYL-CHLORIDE RESIN COMPOSITION, ANTIVIRAL SHEET OF VINYL-CHLORIDE RESIN, PROCESS FOR PRODUCING THE SAME, INTERIOR DECORATIVE SHEET, PROCESS FOR PRODUCING INTERIOR DECORATIVE SHEET, INTERIOR DECORATIVE SHEET OF POLY(VINYL CHLORIDE) RESIN, ANTIVIRAL WALLPAPER, AND PROCESS FOR PRODUCING ANTIVIRAL WALLPAPER

(71) Applicant: Lonseal Corporation, Tokyo (JP)

(72) Inventors: Taro Takahashi, Tsuchiura (JP); Tomohiro Ono, Tsuchiura (JP); Tomoko Terui, Tsuchiura-shi, Ibaraki (JP)

(73) Assignee: LONSEAL CORPORATION, Tokyo (JP)

( * ) Notice: Subject to any disclaimer, the term of this patent is extended or adjusted under 35 U.S.C. 154(b) by 0 days.

(21) Appl. No.: 14/904,414

(22) PCT Filed: Jul. 11, 2014

(86) PCT No.: PCT/JP2014/068588
§ 371 (c)(1),
(2) Date: Jan. 11, 2016

(87) PCT Pub. No.: WO2015/005476
PCT Pub. Date: Jan. 15, 2015

(65) Prior Publication Data
US 2016/0143273 A1  May 26, 2016

(30) Foreign Application Priority Data

Jul. 12, 2013 (JP) .................... 2013-147100
Jul. 12, 2013 (JP) .................... 2013-147101
Jul. 12, 2013 (JP) .................... 2013-147102
Oct. 18, 2013 (JP) .................... 2013-217171
Oct. 18, 2013 (JP) .................... 2013-217421

(51) Int. Cl.
| | |
|---|---|
| A01N 25/34 | (2006.01) |
| A01N 29/02 | (2006.01) |
| B32B 27/20 | (2006.01) |
| B32B 27/22 | (2006.01) |
| B32B 27/30 | (2006.01) |
| C08K 5/42 | (2006.01) |
| C08L 27/06 | (2006.01) |
| E04F 13/00 | (2006.01) |

(52) U.S. Cl.
CPC .............. *C08L 27/06* (2013.01); *A01N 25/34* (2013.01); *A01N 29/02* (2013.01); *B32B 27/20* (2013.01); *B32B 27/22* (2013.01); *B32B 27/304* (2013.01); *C08K 5/42* (2013.01); *E04F 13/002* (2013.01); *B32B 2307/7145* (2013.01); *B32B 2607/02* (2013.01); *C08L 2205/025* (2013.01)

(58) Field of Classification Search
None
See application file for complete search history.

(56) References Cited

U.S. PATENT DOCUMENTS

2009/0035339 A1  2/2009  Istvan et al.
2010/0272668 A1  10/2010  Matsushita et al.

FOREIGN PATENT DOCUMENTS

| | | |
|---|---|---|
| CN | 101050293 A | 10/2007 |
| CN | 101724208 A | 6/2010 |
| CN | 103015218 A | 4/2013 |
| JP | 53-80470 A | 7/1978 |
| JP | 4-241173 A | 8/1992 |
| JP | 4-337345 A | 11/1992 |
| JP | 4-357031 A | 12/1992 |
| JP | 8-217938 A | 8/1996 |
| JP | 8-259761 A | 10/1996 |
| JP | 9-143326 A | 6/1997 |
| JP | 9-235460 A | 9/1997 |
| JP | 9-309935 A | 12/1997 |
| JP | 10-204241 A | 8/1998 |
| JP | 2004-195863 A | 7/2004 |
| JP | 3973234 B2 | 9/2007 |
| JP | 2009-127163 A | 6/2009 |
| JP | 2010-024587 A | 2/2010 |
| JP | 2010-505964 A | 2/2010 |
| JP | 4584339 B2 | 11/2010 |
| JP | 2011-088965 A | 5/2011 |
| JP | 2011-152102 A | 8/2011 |
| WO | 98/46654 A1 | 10/1998 |
| WO | 2011/145083 A2 | 11/2011 |

OTHER PUBLICATIONS

Machine translation, WO 98/46654 (1998).*
Machine translation, JP-04241173A (1992).*
Chinese Office Action dated Dec. 14, 2016, for corresponding CN Application No. 201480039824.8, with English Translation, 23 pages.
Extended Search Report from European Patent Office dated Feb. 3, 2017, issued in corresponding European Application No. 14822191.4 (6 pages).

(Continued)

*Primary Examiner* — Bethany P Barham
*Assistant Examiner* — Barbara S Frazier
(74) *Attorney, Agent, or Firm* — Seed IP Law Group LLP

(57) ABSTRACT

There is provided an antiviral vinyl-chloride-based resin composition including: 100 parts by weight of a poly(vinyl chloride)-based resin obtained by mixing 10-90 parts by weight of a vinyl-chloride-based resin for paste with 90-10 parts by weight of a suspension vinyl-chloride-based resin; and 0.5-10.0 parts by weight of a sulfonic-acid-based surfactant.

10 Claims, No Drawings

(56) References Cited

OTHER PUBLICATIONS

International Search Report, dated Oct. 14, 2014, for International Application No. PCT/JP2014/068588, 4 pages. (with English Translation).
Written Opinion, dated Oct. 14, 2014, for International Application No. PCT/JP2014/068588, 5 pages.
English Translation of the Written Opinion, dated Oct. 14, 2014, for International Application No. PCT/JP2014/068588, 7 pages.
Japanese Office Action, dated Jul. 7, 2017, for Japanese Application No. 2013-217171, 6 pages (with English Machine Translation).
Japanese Office Action, dated May 22, 2017, for Japanese Application No. 2013-217421, 4 pages (with English Machine Translation).
Japanese Office Action, dated Jun. 11, 2017, for Japanese Application No. 2013-147101, 7 pages (with English Machine Translation).
Chinese Office Action, dated Nov. 3, 2017, for Chinese Application No. 201480039824.8, 25 pages, (with English translation).
Japanese Office Action, dated Feb. 15, 2018, for Japanese Application No. 2013-217171, 9 pages (with English machine translation).
Japanese Office Action, dated Apr. 5, 2018, for Japanese Application No. 2014-142542, 6 pages. (With English Machine Translation).
Japanese Office Action, dated Apr. 5, 2018, for Japanese Application No. 2014-142609, 6 pages. (With English Machine Translation).
Office Action dated Jun. 13, 2018, for corresponding Japanese Application No. JP2013-217171 and English translation thereof (6 pages).

* cited by examiner

ANTIVIRAL VINYL-CHLORIDE RESIN COMPOSITION, ANTIVIRAL SHEET OF VINYL-CHLORIDE RESIN, PROCESS FOR PRODUCING THE SAME, INTERIOR DECORATIVE SHEET, PROCESS FOR PRODUCING INTERIOR DECORATIVE SHEET, INTERIOR DECORATIVE SHEET OF POLY(VINYL CHLORIDE) RESIN, ANTIVIRAL WALLPAPER, AND PROCESS FOR PRODUCING ANTIVIRAL WALLPAPER

TECHNICAL FIELD

The present invention in a first aspect thereof relates to an antiviral vinyl-chloride-based resin composition, an antiviral vinyl-chloride-based resin sheet obtained by forming the composition, and a process for producing an antiviral shaped object of a vinyl-chloride-based resin.

The invention in second and third aspects thereof relates to an interior decorative sheet and a process for producing the interior decorative sheet.

The invention in the third aspect relates to an interior decorative sheet of a poly(vinyl chloride)-based resin.

The invention in a fourth aspect thereof relates to an interior decorative sheet excellent in terms of antiviral property and antifouling property.

The invention in a fifth aspect thereof relates to an antiviral wallpaper which inactivates various viruses, and to a process for producing the antiviral wallpaper.

BACKGROUND ART

Viral diseases caused by serious acute respiratory syndrome (SARS) virus, avian influenza viruses, foot-and-mouth disease virus, new kinds of influenza viruses, etc. arouse social problems one after another. Originally, viruses have limited host ranges, and it is usual for some viruses to infect mammals only and for other viruses to infect birds only. However, avian influenza viruses have a wide range of hosts and can infect not only birds but also mammals, and there is hence a possibility that some avian influenza viruses might infect human beings also. At present, avian influenza virus type H5N1 infests Asia and Europe, and there is a fear that a virulent influenza virus may appear as a result of a variation of that type of virus as a base to cause a pandemic.

There is hence a desire for development of a material which shows antiviral properties or a material capable of imparting antiviral properties, as a measure against such a pandemic. In addition, antiviral products for not only medical facilities such as hospitals, health centers, and protective institutions but also general public facilities and even families have come to be desired in preparation for a viral pandemic.

Patent document 1 discloses a sheet obtained by mixing a composition for imparting antiviral properties which includes either regenerated collagen fibers or a regenerated collagen powder with a polyurethane resin and coating a flexible PVC sheet with the mixture.

According to the definite cases concerning countries and human beings of the occurrence of avian influenza (H5N1) reported by the Ministry of Health, Labor and Welfare of Japan, highly pathogenic avian influenza has occurred in a wide range of regions including Asia, Europe, the Middle East, and Africa since November, 2003. Infections of avian influenza which have been ascertained include not only ones from fowls to fowls but also ones from fowls to primates. With respect to human beings, in particular, six hundred and odd persons were infected so far and at least 350 of these died. Furthermore, there is a possibility that avian influenza viruses might undergo a variation through crossing with a human influenza virus or even by themselves to become virulent.

Consequently, techniques and products which are capable of rapidly inactivating viruses are eagerly desired. Of such products, interior decorative building materials for use in, for example, medical facilities, which are expected to undergo contacts with viruses, are especially desired to inactivate viruses. In particular, wallpapers, which occupy a large part of construction areas, are highly desired to have antiviral properties.

For wallpapers, vinyl-chloride-based resins such as vinyl chloride resins and olefin-based resins are frequently used. In particular, vinyl-chloride-based resins are used for most wallpapers because vinyl-chloride-based resins are inexpensive and have various excellent properties and because the wallpapers thereof can be made to have an attractive appearance by embossing the wallpapers to form fine recesses and protrusions in the surfaces thereof.

Meanwhile, patent document 2 proposes a method in which a vinyl/maleic anhydride copolymer to which metal ions have been fixed is used as a material for imparting antiviral properties to fibers. However, there is no statement therein concerning any technique for applying the invention to a wallpaper constituted of a poly(vinyl chloride)-based resin or to an interior decorative sheet.

An antiviral agent is an agent which deprives viruses of the infectivity and thereby prevents the viruses from invading cells. Known as such an antiviral agent is, for example, slaked lime. In patent document 3, a resinous coating film containing slaked lime is disclosed.

CITATION LIST

Patent Documents

Patent Document 1: JP-A-2009-127163
Patent Document 2: Japanese Patent No. 4584339
Patent Document 3: JP-A-2011-152102

SUMMARY OF THE INVENTION

Problems that the Invention is to Solve

The present inventors discovered that a poly(vinyl chloride)-based resin composition including a poly(vinyl chloride)-based resin and a sulfonic-acid-based surfactant exhibits high antiviral performance. However, there have been cases where poly(vinyl chloride)-based resin compositions containing a sulfonic-acid-based surfactant are prone to suffer initial discoloration upon heating when formed, resulting in discolored shaped objects.

Under these circumstances, an object of the invention, in a first aspect thereof, is to provide an antiviral vinyl-chloride-based resin composition which has excellent antiviral properties and has improved insusceptibility to discoloration due to forming, in particular, to initial discoloration, and an antiviral sheet.

In the case where a poly(vinyl chloride)-based resin composition containing a sulfonic-acid-based surfactant is formed by melt shaping, coloring is prone to occur due to the heating. There have hence been cases where the resultant interior decorative sheets have yellowed. There have also been cases where the composition sticks to the rolls when processed by roll processing or the like.

Under such circumstances, the present invention in a second aspect thereof provides an antiviral interior decorative sheet which has excellent antiviral properties and improved unsusceptibility to coloring due to forming and which has improved processability.

The present inventors discovered that an interior decorative poly(vinyl chloride)-based resin sheet formed from a poly(vinyl chloride)-based sol composition containing a sulfonic-acid-based surfactant can rapidly reduce the virus titer in contact therewith and inactivate the viruses. However, the inventors have discovered that the addition of a sulfonic-acid-based surfactant during the production of a poly(vinyl chloride)-based sol arouses a problem in that the surfactant has poor dispersibility in the poly(vinyl chloride)-based resin and the interior decorative sheet of this poly(vinyl chloride)-based resin undesirably has a rugged surface, resulting in an appearance failure.

Under such circumstances, an object of the invention, in a third aspect thereof, is to provide an interior decorative sheet having an excellent appearance and formed from an antiviral poly(vinyl chloride)-based sol composition having excellent antiviral properties.

Meanwhile, general interior decorative sheets are used in such a manner that after application of the sheets, an antifouling treatment as a measure against fouling is performed by, for example, applying a wax thereto. Because of this, there have been cases where even an interior decorative sheet which itself has sufficient antiviral properties undesirably comes to have insufficient antiviral properties due to the waxing. Consequently, from the standpoint of making an interior decorative sheet exhibit the antiviral properties, waxing should be avoided, resulting in the possibility of insufficient antifouling properties.

Under such circumstances, an object of the invention, in a fourth aspect thereof, is to provide an interior decorative sheet which is excellent in terms of antiviral property and antifouling property.

The present inventors discovered that a wallpaper based on poly(vinyl chloride) containing a sulfonic-acid-based surfactant can rapidly reduce the virus titer in contact therewith and inactivate the viruses. However, the inventors have discovered that the addition of a sulfonic-acid-based surfactant during wallpaper production arouses a new problem in that the surfactant has poor dispersibility in the poly(vinyl chloride) resin to cause appearance failures, e.g., rumples, in the wallpaper surface.

An object of the invention, in a fifth aspect thereof, is to provide an antiviral wallpaper which has an excellent appearance and which rapidly reduces the virus titer in contact therewith and inactivates the viruses.

Means for Solving the Problems

[First Aspect]

A means which the first aspect of the invention employs for overcoming the problems described above is to provide an antiviral vinyl-chloride-based resin composition which is a mixture of a vinyl-chloride-based resin for paste, a suspension vinyl-chloride-based resin, and a sulfonic-acid-based surfactant.

More specifically, the means is to provide an antiviral vinyl-chloride-based resin composition characterized by including: 100 parts by weight of a poly(vinyl chloride)-based resin obtained by mixing 10-90 parts by weight of a vinyl-chloride-based resin for paste with 90-10 parts by weight of a suspension vinyl-chloride-based resin; and 0.5-10.0 parts by weight of a sulfonic-acid-based surfactant.

The antiviral vinyl-chloride-based resin composition may be one in which the poly(vinyl chloride)-based resin is a resin obtained by mixing the vinyl-chloride-based resin for paste to which the sulfonic-acid-based surfactant has been added with the suspension vinyl-chloride-based resin.

It is preferable that the antiviral vinyl-chloride-based resin composition should be one in which the sulfonic-acid-based surfactant was added during the production of the vinyl-chloride-based resin for paste.

These antiviral vinyl-chloride-based resin compositions each can be formed into an antiviral vinyl-chloride-based resin sheet.

Furthermore, use can be made of a process for producing an antiviral shaped object of a vinyl-chloride-based resin, the process including a step in which 10-90 parts by weight of a vinyl-chloride-based resin for paste is mixed with 90-10 parts by weight of a suspension vinyl-chloride-based resin and a step in which the poly(vinyl chloride)-based resin including the vinyl-chloride-based resin for paste and the suspension vinyl-chloride-based resin is melt-shaped, wherein the vinyl-chloride-based resin for paste contains a sulfonic-acid-based surfactant, and the sulfonic-acid-based surfactant has been added in an amount of 0.5-10.0 parts by weight per 100 parts by weight of the poly(vinyl chloride)-based resin.

Use can also be made of a process for producing an antiviral vinyl-chloride-based resin sheet, the process including a step in which 10-90 parts by weight of a vinyl-chloride-based resin for paste is mixed with 90-10 parts by weight of a suspension vinyl-chloride-based resin and a step in which the poly(vinyl chloride)-based resin including the vinyl-chloride-based resin for paste and the suspension vinyl-chloride-based resin is formed into a sheet, wherein the vinyl-chloride-based resin for paste contains a sulfonic-acid-based surfactant, and the sulfonic-acid-based surfactant has been added in an amount of 0.5-10.0 parts by weight per 100 parts by weight of the poly(vinyl chloride)-based resin.

[Second Aspect]

A means which the second aspect of the invention employs for overcoming the problems described above is to provide an interior decorative sheet including an antiviral poly(vinyl chloride)-based resin composition which is a mixture of: a poly(vinyl chloride)-based resin that is a mixture of a poly(vinyl chloride)-based resin for paste and a suspension poly(vinyl chloride)-based resin; a sulfonic-acid-based surfactant; and a plasticizer.

More specifically, the means is to provide an interior decorative sheet including a surface layer constituted of an antiviral poly(vinyl chloride)-based resin composition which includes: 100 parts by weight of a poly(vinyl chloride)-based resin including 10-90 parts by weight of a poly(vinyl chloride)-based resin for paste and 90-10 parts by weight of a suspension poly(vinyl chloride)-based resin; 0.5-10.0 parts by weight of a sulfonic-acid-based surfactant; and 10-100 parts by weight of a plasticizer.

The interior decorative sheet can be one in which the poly(vinyl chloride)-based resin is a mixture of the suspension poly(vinyl chloride)-based resin with the poly(vinyl chloride)-based resin for paste to which the sulfonic-acid-based surfactant has been added.

Furthermore, the interior decorative sheet may be one in which the sulfonic-acid-based surfactant was added during the production of the poly(vinyl chloride)-based resin for paste.

Provided as a production process is a process for producing an interior decorative sheet including an antiviral poly(vinyl chloride)-based resin composition including 100 parts by weight of a poly(vinyl chloride)-based resin including 10-90 parts by weight of a poly(vinyl chloride)-based resin for paste and 90-10 parts by weight of a suspension poly(vinyl chloride)-based resin, 0.5-10.0 parts by weight of a sulfonic-acid-based surfactant, and 10-100 parts by weight of a plasticizer, the process including a step in which the poly(vinyl chloride)-based resin for paste that contains the sulfonic-acid-based surfactant is mixed with the suspension poly(vinyl chloride)-based resin to obtain the poly(vinyl chloride)-based resin, a step in which the poly(vinyl chloride)-based resin is mixed with the plasticizer to obtain the antiviral poly(vinyl chloride)-based resin composition, and a step in which the antiviral poly(vinyl chloride)-based resin composition is melt-shaped.

[Third Aspect]

A means which the third aspect of the invention employs for overcoming the problems described above essentially is to apply a poly(vinyl chloride)-based sol composition including a poly(vinyl chloride)-based resin for paste which contains a given amount of a sulfonic-acid-based surfactant and further including a plasticizer.

Specifically, the means is one wherein an antiviral poly(vinyl chloride)-based sol composition which includes 100 parts by weight of a poly(vinyl chloride)-based resin for paste, 0.1-7.5 parts by weight of a sulfonic-acid-based surfactant, and a plasticizer and in which the sulfonic-acid-based surfactant was added during the production of the poly(vinyl chloride)-based resin for paste is applied to a surface of a base to produce an interior decorative sheet made of a poly(vinyl chloride)-based resin.

[Fourth Aspect]

A means which the fourth aspect of the invention employs for overcoming the problems described above is to provide an interior decorative sheet including a surface layer, characterized in that the surface layer is constituted of a poly(vinyl chloride)-based resin composition including 100 parts by weight of a poly(vinyl chloride)-based resin, 0.1-10.0 parts by weight of a sulfonic-acid-based surfactant, 10-50 parts by weight of a plasticizer, and 1-20 parts by weight of a silicone-based copolymer.0

The poly(vinyl chloride)-based interior decorative sheet may be one in which the poly(vinyl chloride)-based resin in the surface layer includes 100-1 part by weight of a vinyl-chloride-based resin for paste and 0-99 parts by weight of a suspension vinyl-chloride-based resin, or may be one in which the vinyl-chloride-based resin for paste contains the sulfonic-acid-based surfactant or in which the resin composition constituting the surface layer contains a filler in an amount of 1-50 parts by weight.

[Fifth Aspect]

The present inventors diligently made investigations on methods of adding a sulfonic-acid-based surfactant in order to overcome the problems. As a result, the inventors have discovered that an antiviral wallpaper having an intact appearance is satisfactorily obtained in cases when a vinyl chloride resin for paste to which a sulfonic-acid-based surfactant has been added beforehand is used to produce the wallpaper.

Specifically, provided is an antiviral wallpaper including a base layer and a resin layer including a resinous ingredient that includes a vinyl chloride resin for paste into which a sulfonic-acid-based surfactant has been incorporated beforehand in an amount of 1.2% by weight or larger.

Effects of the Invention

According to the first aspect of the invention, it is possible to obtain an antiviral vinyl-chloride-based resin composition and an antiviral sheet which have excellent antiviral properties and improved unsusceptibility to discoloration during forming, in particular, to initial discoloration.

According to the second aspect of the invention, it is possible to obtain an antiviral interior decorative sheet having excellent antiviral properties, improved unsusceptibility to coloring during forming, and improved processability, and to obtain a process for producing the interior decorative sheet.

According to the third aspect of the invention, it is possible to obtain an interior decorative sheet which is made of a poly(vinyl chloride)-based resin and is excellent in terms of antiviral property and appearance.

According to the fourth aspect of the invention, it is possible to obtain an interior decorative sheet which is excellent in terms of antiviral property and antifouling property. This interior decorative sheet of the invention is less apt to suffer the adhesion of fouling substances thereto, and the fouling substance, if having adhered thereto, can be removed by simple cleaning. Because of this, the interior decorative sheet can be used without necessitating an antifouling treatment such as waxing, and can hence sufficiently exhibit the antiviral properties. In cases when a vinyl-chloride-based resin for paste which contains a sulfonic-acid-based surfactant is used for forming the surface layer, the interior decorative sheet can be made to be inhibited from suffering resin coloring and to have an excellent appearance and even better antiviral properties. Furthermore, by incorporating a filler into the surface layer in an amount of 1-50 parts by weight, the processability is further improved.

According to the fifth aspect of the invention, it is possible to obtain an antiviral wallpaper and a process for producing the antiviral wallpaper.

The antiviral wallpaper according to the fifth aspect of the invention reduces the virus titer and inactivates viruses in a short time period after the wallpaper comes into contact with the viruses, and has an excellent appearance.

MODES FOR CARRYING OUT THE INVENTION

The present invention is described below in detail.

In the invention, the term "vinyl-chloride-based resin for paste" means fine polymer particles having a particle diameter of 0.02-20.0 μm and obtained mainly by an emulsion polymerization method or a microsuspension polymerization method. This resin is generally characterized by becoming pasty upon addition of a plasticizer thereto.

For producing a vinyl-chloride-based resin for paste, any production process can be used so long as a vinyl-chloride-based resin for paste can be obtained thereby. Examples of most common processes include: an emulsion polymerization method in which a vinyl-chloride-based monomer is polymerized together with deionized water, an emulsifying agent, and a water-soluble polymerization initiator with gentle stirring; a seed emulsion polymerization method in which the particles obtained by the emulsion polymerization method are used as seeds to conduct emulsion polymerization; a microsuspension polymerization method in which a vinyl-chloride-based monomer is mixed with deionized water, an emulsifying agent optionally together with an emulsifying aid such as a higher alcohol, and an oil-soluble polymerization initiator by means of a homogenizer or the like to disperse the ingredients and the monomer is then polymerized with gentle stirring; and a seed microsuspension polymerization method in which the seeds containing the oil-soluble polymerization initiator and obtained by the microsuspension polymerization method are used to conduct polymerization. In each of these methods, polymerization is conducted at a temperature of 30-80° C. and the latex obtained is spray-dried and then pulverized. As such, the production of a vinyl-chloride-based resin for paste includes a polymerization step, in which polymerization is conducted, and subsequent post-polymerization steps.

The term "suspension vinyl-chloride-based resin" means a vinyl-chloride-based resin which is polymer particles having a particle diameter of about 50-200 μm and obtained mainly by a suspension polymerization method and which has a porous indefinite shape. Due to the porous shape, this vinyl-chloride-based resin can absorb liquids such as plasticizers and can hence be prevented from becoming pasty.

[First Aspect]

An embodiment of the first aspect of the invention is an antiviral vinyl-chloride-based resin composition characterized by including: 100 parts by weight of a poly(vinyl chloride)-based resin obtained by mixing 10-90 parts by weight of a vinyl-chloride-based resin for paste with 90-10 parts by weight of a suspension vinyl-chloride-based resin; and 0.5-10.0 parts by weight of a sulfonic-acid-based surfactant.

This antiviral vinyl-chloride-based resin composition exhibits antiviral properties since a given amount of a sulfonic-acid-based surfactant has been added to the poly (vinyl chloride)-based resin. From the standpoint of enabling the composition to exhibit higher antiviral properties and to be inhibited from suffering initial discoloration during forming, it is preferable that the sulfonic-acid-based surfactant should have been added beforehand to the vinyl-chloride-based resin for paste. Namely, it is preferred to add the sulfonic-acid-based surfactant during the production of the vinyl-chloride-based resin for paste. In this connection, it is possible to add a sulfonic-acid-based surfactant as, for example, an emulsifying agent in a polymerization step. Such addition of a sulfonic-acid-based surfactant may result in cases where a vinyl-chloride-based resin for paste which has desired properties is not obtained due to the influence of the sulfonic-acid-based surfactant added.

Meanwhile, a sulfonic-acid-based surfactant can be added also in a post-polymerization step. It is noted that sulfonic-acid-based surfactants are water-soluble, and that in cases when a vinyl chloride resin for paste is produced by emulsion polymerization or seed emulsion polymerization, a latex including water as the medium is obtained as an intermediate form of the product of polymerization. Consequently, by adding a sulfonic-acid-based surfactant to this latex, the sulfonic-acid-based surfactant is satisfactorily dispersed into the vinyl chloride resin. By thus adding a sulfonic-acid-based surfactant to the latex resulting from polymerization, a vinyl chloride resin for paste which has desired properties is obtained while avoiding influences on the polymerization conditions. Thus, the effect of attaining both high antiviral properties and inhibition of initial discoloration during forming can be more efficiently obtained.

This effect of attaining both high antiviral properties and inhibition of initial discoloration is thought to be attributable to the sulfonic-acid-based surfactant which comes into the state of having been finely dispersed in the vinyl-chloride-based resin for paste.

Namely, the finely dispersed state of the sulfonic-acid-based surfactant enables the antiviral properties to be exhibited more efficiently. It is presumed that the addition amount of the sulfonic-acid-based surfactant, which enhances initial discoloration during forming, can hence be reduced and, as a result, the discoloration during forming can be mitigated.

The average degree of polymerization of the poly(vinyl chloride)-based resin for paste is not particularly limited so long as forming is substantially possible. However, the average degree of polymerization thereof is preferably in the range of 500-2,000, more preferably in the range of 700-1,300. In case where the average degree of polymerization thereof is less than 500, the composition is difficult to process because the melt viscosity thereof is low. In case where the average degree of polymerization thereof exceeds 2,000, there is a possibility that the composition might be difficult to process because of the high melt viscosity thereof.

In cases when a poly(vinyl chloride)-based resin for paste is used, the resultant resin composition has poor handleability before thermal melting, since the poly(vinyl chloride)-based resin for paste has the property of becoming pasty at ordinary temperature when mixed with a liquid such as a plasticizer. In the case where the resin composition is formed by a melt shaping method in which the resin composition is thermally melted, kneaded, shaped, and then solidified by cooling, it is preferred to blend the resin with a suspension vinyl-chloride-based resin. As such melt shaping methods, there are forming methods involving an extrusion step, calendering step, or the like. Examples thereof include extrusion molding, injection molding, blow molding, calendering, and roll processing.

A more detailed explanation is given below. The poly (vinyl chloride)-based resin for paste which has become pasty due to addition of a plasticizer or the like is a liquid having flowability. Since the machine equipment for melt shaping methods has been designed to be suitable for introduction of solids such as pellets and powders thereinto, liquids such as pastes cannot generally be used because of leakage, etc. Furthermore, the machines for use in the step of heating and kneading have been optimized so as to be capable of melting and kneading solids such as pellets and powders. In case where a liquid is used in these machines, a problem may arise in, for example, that the material is not sufficiently kneaded.

Consequently, in the case of using a poly(vinyl chloride)-based resin for paste, the antiviral vinyl-chloride-based resin composition can be rendered easily formable by the melt shaping method, by blending the resin with a suspension vinyl-chloride-based resin to give a solid resin composition.

As described above, high antiviral properties and prevention of initial discoloration during processing can be attained by using a poly(vinyl chloride)-based resin for paste to which a sulfonic-acid-based surfactant was added during the production of the vinyl-chloride-based resin, and an antiviral vinyl-chloride-based resin composition which shows improved handleability and processability in melt shaping methods is obtained by mixing the poly(vinyl chloride)-based resin for paste with a suspension vinyl-chloride-based resin.

The blending ratio between the vinyl-chloride-based resin for paste and the suspension vinyl-chloride-based resin is not particularly limited so long as the sulfonic-acid-based surfactant is contained in an amount of 0.5-10.0 parts by weight per 100 parts by weight of the poly(vinyl chloride)-based resin (sum of the vinyl-chloride-based resin for paste and the suspension vinyl-chloride-based resin), i.e., based on the whole poly(vinyl chloride)-based resin, and so long as the composition can be formed without arousing a problem. However, the amounts of the vinyl-chloride-based resin for paste and the suspension vinyl-chloride-based resin are preferably 90-10 parts by weight and 10-90 parts by weight, respectively. More preferably, the amounts of the vinyl-chloride-based resin for paste and the suspension vinyl-chloride-based resin are 70-20 parts by weight and 30-80 parts by weight, respectively. Even more preferably, the amounts of the vinyl-chloride-based resin for paste and the suspension vinyl-chloride-based resin are 50-20 parts by weight and 50-80 parts by weight, respectively.

The average degree of polymerization of the suspension poly(vinyl chloride)-based resin is not particularly limited so long as forming is substantially possible. However, the average degree of polymerization thereof is preferably in the range of 500-2,000, more preferably in the range of 700-1,300. In case where the average degree of polymerization thereof is less than 500, the composition is difficult to process because the melt viscosity thereof is low. In case where the average degree of polymerization thereof exceeds 2,000, there is a possibility that the composition might be difficult to process because of the high melt viscosity thereof.

Examples of the sulfonic-acid-based surfactant to be used in the invention include alkylbenzenesulfonic acid compounds, (alkyldiphenyl ether)disulfonic acid compounds, alkylnaphthalenesulfonic acid compounds, alkylsulfuric acid ester compounds, polyoxyethylene alkylsulfuric acid ester compounds, and naphthalenesulfonic acid/formalin condensate compounds. Preferred of these, from the standpoint of excellent antiviral properties, are alkylbenzenesulfonic acid compounds, (alkyldiphenyl ether)disulfonic acid compounds, and alkylnaphthalenesulfonic acid compounds. More preferred are alkylbenzenesulfonic acid compounds, which are especially superior in antiviral property.

In the sulfonic-acid-based surfactant to be used in the invention, the sulfo group has a high affinity for, for example, the neuraimidase of influenza viruses and can exert an inhibitory action thereon. With respect to the structure of the functional group, the structure thereof affects approach to the neuraimidase and it is important that the structure thereof should be not bulky so that the neuraimidase is less apt to suffer steric hindrance. In this respect, alkylbenzenesulfonic-acid-based surfactants are suitable, and dodecylbenzenesulfonic-acid-based surfactants are especially preferred.

Furthermore, preferred as the sulfonic-acid-based surfactant are sulfonic-acid-salt-based surfactants. Specifically, alkali metal salts such as sodium salts and potassium salts and salts with alkaline earth metals such as calcium and barium are suitable for use. Especially preferred is sodium dodecylbenzenesulfonate (DBS).

A plurality of sulfonic-acid-based surfactants may be added unless the antiviral properties are lessened thereby, and there are no limitations on addition of other kinds of surfactants.

From the standpoint of imparting antiviral properties, a sulfonic-acid-based surfactant is added in an amount of 0.5-10.0 parts by weight per 100 parts by weight of the poly(vinyl chloride)-based resin.

The amount thereof is preferably 0.5-7.0 parts by weight, more preferably 1.5-7.0 parts by weight, even more preferably 1.5-4.2 parts by weight. In case where the amount thereof is less than 0.5 parts by weight, the antiviral vinyl-chloride-based resin sheet obtained has poor antiviral properties. In case where the amount thereof exceeds 10.0 parts by weight, the composition is difficult to process.

In the case of adding a sulfonic-acid-based surfactant to a poly(vinyl chloride)-based resin for paste, the content of the sulfonic-acid-based surfactant based on the sum of the poly(vinyl chloride) resin for paste and the sulfonic-acid-based surfactant is preferably 0.1-15% by weight, more preferably 0.7-10% by weight, especially preferably 1.0-7.5% by weight. In case where the content thereof is less than 0.1% by weight, the antiviral vinyl-chloride-based resin sheet obtained has poor antiviral properties. When the content thereof exceeds 15% by weight, there are cases where the efficiency of the production of this vinyl-chloride-based resin for paste becomes poor.

A plasticizer can be added for the purpose of improving the flexibility and processability. Examples thereof include plasticizers based on esters of aliphatic dibasic acids, such as phthalic-ester-based plasticizers, e.g., DOP (di-2-ethylhexyl phthalate), DINP (diisononyl phthalate), and DIDP (diisodecyl phthalate), adipic-ester-based plasticizers, e.g., DOA (di-2-ethylhexyl adipate) and DIDA (diisodecyl adipate), sebacic-ester-based plasticizers, e.g., DOS (di-2-ethylhexyl sebacate), and azelaic-ester-based plasticizers, e.g., DOZ (di-2-ethylhexyl azelate), phosphoric-ester-based plasticizers such as tricresyl phosphate, trixylenyl phosphate, cresyl diphenyl phosphate, tris(isopropylphenyl) phosphate, and tris(dichloropropyl) phosphate, polyester-based plasticizers, epoxy-based plasticizers, and sulfonic-ester-based plasticizers. Examples of plasticizers having satisfactory compatibility with vinyl-chloride-based resins include phthalic-ester-based plasticizers and polyester-based plasticizers having a high molecular weight. One plasticizer may be used alone, or plasticizers of multiple kinds may be used in combination.

It is preferable that the amount of the plasticizer to be added should be 10-50 parts by weight per 100 parts by weight of the vinyl-chloride-based resins. In case where the addition amount of the plasticizer exceeds 50 parts by weight, the resultant resin composition is prone to become pasty and may have poor handleability before thermal melting. In case where the amount thereof is less than 10 parts by weight, there is a possibility that the resultant resin composition is difficult to process. The amount of the plasticizer to be added is preferably 10-40 parts by weight, more preferably 20-40 parts by weight.

It is noted here that flexible poly(vinyl chloride) resin compositions having a plasticizer content of approximately 10 parts or higher have higher antiviral properties than rigid poly(vinyl chloride) resin compositions having a plasticizer content of approximately less than 10 parts in the case where a sulfonic-acid-based surfactant has been added to both in the same amount. Namely, an antiviral effect is apt to be obtained with flexible poly(vinyl chloride) resin compositions.

A filler can be added to the antiviral vinyl-chloride-based resin composition for the purpose of improving the processability. As the filler, use can be made of calcium carbonate, silica, and other inorganic fillers such as platy fillers, e.g., talc and mica, clays, e.g., bentonite and calcined kaolin, metal oxides, e.g., magnesium oxide and alumina, and metal hydroxides, e.g., magnesium hydroxide and aluminum hydroxide. Any of various surface treatments with fatty acids, modified fatty acids, etc. may have been given to the filler in order to enhance the affinity for vinyl-chloride-based resins.

It is preferable that the amount of the filler to be added should be 1-50 parts by weight per 100 parts by weight of the vinyl-chloride-based resins. When the addition amount of the filler exceeds 50 parts by weight, there are cases where shaped objects, such as sheets, obtained by forming the antiviral vinyl-chloride-based resin composition have poor surface smoothness. Meanwhile, when the addition amount thereof is less than 1 part by weight, there are cases where the effect of improving processability is not obtained. The amount of the filler to be added is preferably 5-30 parts by weight, more preferably 10-20 parts by weight. In the case where transparency is necessary, the addition amount of the filler is preferably 1-5 parts by weight.

It is preferred to add an acrylic polymeric processing aid to the antiviral vinyl-chloride-based resin composition for the purpose of improving the processability. Examples of the acrylic polymeric processing aid include acrylic polymeric processing aids such as methyl methacrylate/alkyl acrylate copolymers, e.g., methyl methacrylate/butyl acrylate copolymers.

By adding an acrylic polymeric processing aid, the rotational flow and degassing within the bank during forming by roll processing or calendering are rendered satisfactory and plate-out is inhibited. Consequently, a sheet having a satisfactory appearance is obtained.

Other compounding agents generally added to resins may be added according to need, such as ultraviolet absorbers, light stabilizers, ultraviolet-screening agents, antistatic agents, flame retardants, thickeners, surfactants, fluorescent agents, crosslinking agents, and impact modifiers.

The antiviral vinyl-chloride-based resin composition can be produced by mixing a vinyl-chloride-based resin for paste, a suspension vinyl-chloride-based resin, and a sulfonic-acid-based surfactant using a known production device. For example, the composition can be produced by evenly mixing a vinyl-chloride-based resin for paste, a suspension vinyl-chloride-based resin, and a sulfonic-acid-based surfactant by means of a high-speed stirrer, low-speed stirrer, Henschel mixer, or the like. The antiviral vinyl-chloride-based resin composition can be obtained also by subjecting the mixture obtained through mixing to melt mixing by means of a batch heading mixer, Banbury mixer, Kokneader, extruder, or the like. Furthermore, the mixture obtained through the melt mixing may be temporarily pelletized to obtain the antiviral vinyl-chloride-based resin composition as pellets. Incidentally, additives including a plasticizer, stabilizer, and filler can be added at will in accordance with intended uses.

In the case where a sulfonic-acid-based surfactant is added during the production of a vinyl-chloride-based resin for paste, the antiviral vinyl-chloride-based resin composition is obtained by mixing a suspension vinyl-chloride-based resin with the vinyl-chloride-based resin for paste to which the sulfonic-acid-based surfactant has been added. These vinyl-chloride-based resins may be melt-mixed in the same manner as described above, and the mixture may be pelletized.

By melt-shaping the antiviral vinyl-chloride-based resin composition, an antiviral shaped object of a vinyl-chloride-based resin can be obtained. More specifically, an antiviral shaped object of a vinyl-chloride-based resin can be produced by a production process including a step in which 10-90 parts by weight of a vinyl-chloride-based resin for paste is mixed with 90-10 parts by weight of a suspension vinyl-chloride-based resin and a step in which the poly(vinyl chloride)-based resin including the vinyl-chloride-based resin for paste and the suspension vinyl-chloride-based resin is melt-shaped, wherein the vinyl-chloride-based resin for paste contains a sulfonic-acid-based surfactant. The antiviral shaped object of a vinyl-chloride-based resin thus obtained can be used in various applications. For use in interior decorative applications, the shaped object can be used as an antiviral vinyl-chloride-based resin sheet from the standpoint that the surface can be made antiviral over a large area.

The antiviral vinyl-chloride-based resin sheet may be constituted of a single layer or may have a multilayer structure composed of a plurality of layers. It is preferable that the antiviral vinyl-chloride-based resin sheet should include at least the antiviral vinyl-chloride-based resin sheet as the outermost surface. Meanwhile, layers formed by printing or coating-fluid application may be disposed on the surfaces of the antiviral vinyl-chloride-based resin sheet so long as the antiviral properties are exhibited.

In the case of a multilayer structure, the layers to be superposed are not particularly limited. For example, a poly(vinyl chloride)-based resin layer, a layer of another thermoplastic resin, any of various foamed resin layers, a design layer such as a printed layer or colored layer, a base layer such as woven fabric or nonwoven fabric, and the like can be superposed on a layer constituted of the antiviral vinyl-chloride-based resin composition, in accordance with intended uses and required properties.

The antiviral vinyl-chloride-based resin sheet can be produced by a production process including a step in which 10-90 parts by weight of a vinyl-chloride-based resin for paste is mixed with 90-10 parts by weight of a suspension vinyl-chloride-based resin and a step in which the poly(vinyl chloride)-based resin including the vinyl-chloride-based resin for paste and the suspension vinyl-chloride-based resin is melt-shaped by calendering, roll processing, or the like, wherein the vinyl-chloride-based resin for paste contains a sulfonic-acid-based surfactant.

For the mixing step in the production of the antiviral vinyl-chloride-based resin sheet, known devices in common use for thermoplastic resins can be utilized. For example, use may be made of a method in which the composition of the invention is evenly mixed by means of a high-speed stirrer, low-speed stirrer, Henschel mixer, or the like, subsequently melt-mixed by means of a batch kneading mixer, Banbury mixer, Kokneader, extruder, or the like, and immediately formed. The composition which has undergone melt mixing may be temporarily pelletized and thereafter formed.

For the step of melt shaping in the production of the antiviral vinyl-chloride-based resin sheet, use can be made of a method of forming a sheet. Preferred as the sheet forming method is calendering or roll processing, from the standpoint of the thickness accuracy of the sheet obtained. From the standpoint of speed, calendering is preferred. Other general sheet forming methods can be used for forming the sheet. Examples thereof include extrusion molding and press molding.

In cases when a vinyl chloride resin for paste is mixed with a plasticizer, the resultant mixture frequently is pasty as stated above. For forming a pasty resin composition into a sheet, a coating machine such as, for example, a paste coater is generally used. In this case, there are limitations on the structure, thickness, and width of the sheet, production rate, etc., and this production method is not always suitable for sheet production. In view of this, the desired antiviral vinyl-chloride-based resin sheet can be produced by using a blend of a vinyl chloride resin for paste with a suspension vinyl chloride resin and using an extruder or calendering machine, which has excellent sheet-forming properties.

[Second Aspect]

Embodiments of the second aspect of the invention are described below in detail.

The antiviral poly(vinyl chloride)-based resin composition exhibits antiviral properties since a given amount of a sulfonic-acid-based surfactant has been added to the poly(vinyl chloride)-based resin. From the standpoint of enabling the composition to exhibit higher antiviral properties and to be inhibited from suffering coloring during forming, it is preferable that the sulfonic-acid-based surfactant should have been added beforehand to the poly(vinyl chloride)-based resin for paste. Namely, it is preferred to add the sulfonic-acid-based surfactant during the production of the poly(vinyl chloride)-based resin for paste. In this connection, it is possible to add a sulfonic-acid-based surfactant as, for example, an emulsifying agent in a polymerization step. Such addition of a sulfonic-acid-based surfactant may result in cases where a poly(vinyl chloride)-based resin for paste which has desired properties is not obtained due to the influence of the sulfonic-acid-based surfactant added.

Meanwhile, a sulfonic-acid-based surfactant can be added also in a post-polymerization step. It is noted that sulfonic-acid-based surfactants are water-soluble, and that in cases when a poly(vinyl chloride)-based resin for paste is produced by emulsion polymerization or seed emulsion polymerization, a latex including water as the medium is obtained as an intermediate form of the product of polymerization. Consequently, by adding a sulfonic-acid-based surfactant to this latex, the sulfonic-acid-based surfactant is satisfactorily dispersed into the vinyl chloride resin. By thus adding a sulfonic-acid-based surfactant to the latex resulting from polymerization, a poly(vinyl chloride)-based resin for paste which has desired properties is obtained while avoiding influences on the polymerization conditions. Thus, the effect of attaining both high antiviral properties and inhibition of coloring during forming can be more efficiently obtained.

This effect of attaining both high antiviral properties and inhibition of coloring is thought to be attributable to the sulfonic-acid-based surfactant which comes into the state of having been finely dispersed in the poly(vinyl chloride)-based resin for paste.

Namely, the finely dispersed state of the sulfonic-acid-based surfactant enables the antiviral properties to be exhibited more efficiently. It is presumed that the addition amount of the sulfonic-acid-based surfactant, which enhances coloring during forming, can hence be reduced and, as a result, the discoloration during forming can be mitigated.

The average degree of polymerization of the poly(vinyl chloride)-based resin for paste is not particularly limited so long as forming is substantially possible. However, the average degree of polymerization thereof is preferably in the range of 500-2,000, more preferably in the range of 700-1,300. In case where the average degree of polymerization thereof is less than 500, the composition is difficult to process because the melt viscosity thereof is low. In case where the average degree of polymerization thereof exceeds 2,000, there is a possibility that the composition might be difficult to process because of the high melt viscosity thereof.

In cases when a poly(vinyl chloride)-based resin for paste is used, the composition can be applied to a surface of a base to obtain an interior decorative sheet, since the poly(vinyl chloride)-based resin for paste has the property of becoming pasty at ordinary temperature when mixed with a liquid such as a plasticizer. However, in cases when a sulfonic-acid-based surfactant has been added to the poly(vinyl chloride)-based resin for paste, the interior decorative sheet obtained by applying the composition is prone to absorb water to blush upon immersion in water or during use in high-humidity places and there are cases where the blushed state remains after drying. In addition, since the poly(vinyl chloride)-based resin for paste becomes pasty, the resin composition has poor handleability before thermal melting.

Consequently, in the case where the resin composition is to be formed by a melt shaping method in which the resin composition is thermally melted, kneaded, shaped, and then solidified by cooling, it is preferred to blend the resin with a suspension poly(vinyl chloride)-based resin. As such melt shaping methods, there are forming methods involving an extrusion step, calendering step, or the like. Examples thereof include extrusion molding, injection molding, blow molding, calendering, and roll processing.

A more detailed explanation is given below. The poly(vinyl chloride)-based resin for paste which has become pasty due to addition of a plasticizer or the like is a liquid having flowability. Since the machine equipment for melt shaping methods has been designed to be suitable for introduction of solids such as pellets and powders thereinto, liquids such as pastes cannot generally be used because of leakage, etc. Furthermore, the machines for use in the step of heating and kneading have been optimized so as to be capable of melting and kneading solids such as pellets and powders. In case where a liquid is used in these machines, a problem may arise in, for example, that the material is not sufficiently kneaded.

Consequently, in the case of using a poly(vinyl chloride)-based resin for paste, the antiviral poly(vinyl chloride)-based resin composition can be rendered easily formable by the melt shaping method, by blending the resin with a suspension poly(vinyl chloride)-based resin to give a solid resin composition.

As described above, high antiviral properties and more effective prevention of coloring during processing can be attained by using a poly(vinyl chloride)-based resin for paste to which a sulfonic-acid-based surfactant was added during the production of the poly(vinyl chloride)-based resin. Furthermore, an antiviral poly(vinyl chloride)-based resin composition which shows improved handleability and processability in melt shaping methods is obtained by mixing the poly(vinyl chloride)-based resin for paste with a suspension poly(vinyl chloride)-based resin.

There are cases where the interior decorative sheet obtained by applying a vinyl-chloride-based sol composition including a poly(vinyl chloride)-based resin for paste which contains a sulfonic-acid-based surfactant in a given amount suffers blushing by the influence of water. This blushing is thought to be a phenomenon in which in cases when the interior decorative sheet is immersed in water or used in high-humidity places, then the sulfonic-acid-based surfactant in the resin absorbs water or dissolves away in the water to thereby blush the sheet. Especially in transparent products, there are cases where such water blushing deprives the products of the transparency. In contrast, the blushing due to water can be inhibited by forming the antiviral poly(vinyl chloride)-based resin composition into an interior decorative sheet by a melt shaping method.

The average degree of polymerization of the suspension poly(vinyl chloride)-based resin is not particularly limited so long as forming is substantially possible. However, the average degree of polymerization thereof is preferably in the range of 500-2,000, more preferably in the range of 700-1,300. In case where the average degree of polymerization thereof is less than 500, the composition is difficult to process because the melt viscosity thereof is low. In case where the average degree of polymerization thereof exceeds 2,000, there is a possibility that the composition might be difficult to process because of the high melt viscosity thereof.

As the sulfonic-acid-based surfactant to be used in the invention, the same sulfonic-acid-based surfactants as in the first aspect can be used. Preferred examples thereof are also the same.

From the standpoint of imparting antiviral properties, a sulfonic-acid-based surfactant is added in an amount of 0.5-10.0 parts by weight per 100 parts by weight of the poly(vinyl chloride)-based resin.

The amount thereof is preferably 0.5-5.0 parts by weight, more preferably 0.8-4.4 parts by weight. In case where the amount thereof is less than 0.5 parts by weight, the antiviral vinyl-chloride-based resin sheet obtained has poor antiviral properties. In case where the amount thereof exceeds 10.0 parts by weight, the composition is difficult to process.

In the case of adding a sulfonic-acid-based surfactant to a poly(vinyl chloride)-based resin for paste, the content of the sulfonic-acid-based surfactant based on the sum of the poly(vinyl chloride) resin for paste and the sulfonic-acid-based surfactant is preferably 0.1-15% by weight, more preferably 0.7-10% by weight, especially preferably 1.0-7.5% by weight. In case where the content thereof is less than 0.1% by weight, the antiviral poly(vinyl chloride)-based resin sheet obtained has poor antiviral properties. When the content thereof exceeds 15% by weight, there are cases where the efficiency of the production of this poly(vinyl chloride)-based resin for paste becomes poor.

As the plasticizer, a common plasticizer can be used. Examples thereof include plasticizers based on esters of aliphatic dibasic acids, such as phthalic-ester-based plasticizers, e.g., DOP (di-2-ethylhexyl phthalate), DINP (di-isononyl phthalate), and DIDP (diisodecyl phthalate), adipic-ester-based plasticizers, e.g., DOA (di-2-ethylhexyl adipate) and DIDA (diisodecyl adipate), sebacic-ester-based plasticizers, e.g., DOS (di-2-ethylhexyl sebacate), and azelaic-ester-based plasticizers, e.g., DOZ (di-2-ethylhexyl azelate), phosphoric-ester-based plasticizers such as tricresyl phosphate, trixylenyl phosphate, cresyl diphenyl phosphate, tris(isopropylphenyl) phosphate, and tris(dichloropropyl) phosphate, polyester-based plasticizers, epoxy-based plasticizers, and sulfonic-ester-based plasticizers. Examples of plasticizers having satisfactory compatibility with poly(vinyl chloride)-based resins include phthalic-ester-based plasticizers and polyester-based plasticizers having a high molecular weight. One plasticizer may be used alone, or plasticizers of multiple kinds may be used in combination.

The amount of the plasticizer to be added is 10-100 parts by weight per 100 parts by weight of the poly(vinyl chloride)-based resins. In case where the addition amount of the plasticizer exceeds 100 parts by weight, the resultant resin composition is prone to become pasty and may have poor handleability before thermal melting. In case where the amount thereof is less than 10 parts by weight, there is a possibility that the resultant resin composition is difficult to process. The amount of the plasticizer to be added is preferably 10-70 parts by weight, more preferably 20-50 parts by weight.

In the case where the interior decorative sheet is for use on floor surfaces, the amount of the plasticizer to be added, per 100 parts by weight of the poly(vinyl chloride)-based resins, is preferably 10-50 parts by weight, more preferably 10-40 parts by weight, most preferably 20-40 parts by weight, from the standpoint of antifouling property. In case where the addition amount of the plasticizer exceeds 50 parts by weight, fouling substances are prone to adhere to the interior decorative sheet formed from the composition, and the adherent fouling substances are difficult to remove by simple cleaning.

It is noted here that flexible poly(vinyl chloride) resin compositions having a plasticizer content of approximately 10 parts by weight or higher have higher antiviral properties than rigid poly(vinyl chloride) resin compositions having a plasticizer content of approximately less than 10 parts by weight in the case where a sulfonic-acid-based surfactant has been added to both in the same amount. Namely, an antiviral effect is apt to be obtained with flexible poly(vinyl chloride) resin compositions.

A filler can be added to the antiviral poly(vinyl chloride)-based resin composition for the purpose of improving the processability. As the filler, use can be made of calcium carbonate, silica, and other inorganic fillers such as platy fillers, e.g., talc and mica, clays, e.g., bentonite and calcined kaolin, metal oxides, e.g., magnesium oxide and alumina, and metal hydroxides, e.g., magnesium hydroxide and aluminum hydroxide. Any of various surface treatments with fatty acids, modified fatty acids, etc. may have been given to the filler in order to enhance the affinity for poly(vinyl chloride)-based resins.

It is preferable that the amount of the filler to be added should be 1-50 parts by weight per 100 parts by weight of the poly(vinyl chloride)-based resins. When the addition amount of the filler exceeds 50 parts by weight, there are cases where shaped objects, such as sheets, obtained by forming the antiviral poly(vinyl chloride)-based resin composition have poor surface smoothness. Meanwhile, when the addition amount thereof is less than 1 part by weight, there are cases where the effect of improving processability is not obtained. The amount of the filler to be added is preferably 5-30 parts by weight, more preferably 10-20 parts by weight. In the case where transparency is necessary, the addition amount of the filler is preferably 1-5 parts by weight.

It is preferred to add an acrylic polymeric processing aid to the antiviral poly(vinyl chloride)-based resin composition for the purpose of improving the processability. Examples of the acrylic polymeric processing aid include acrylic polymeric processing aids such as methyl methacrylate/alkyl acrylate copolymers, e.g., methyl methacrylate/butyl acrylate copolymers.

By adding an acrylic polymeric processing aid, the rotational flow and degassing within the bank during forming by roll processing or calendering are rendered satisfactory and plate-out is inhibited. Consequently, a sheet having a satisfactory appearance is obtained.

Other compounding agents generally added to resins may be added according to need, such as ultraviolet absorbers, light stabilizers, ultraviolet-screening agents, antistatic agents, flame retardants, thickeners, surfactants, fluorescent agents, crosslinking agents, and impact modifiers.

The interior decorative sheet according to an embodiment of the invention may be constituted of a single layer or have a multilayer structure composed of a plurality of layers, so long as the sheet includes the surface layer. By disposing the surface layer constituted of the antiviral poly(vinyl chloride)-based resin composition so as to form the outermost surface, the interior decorative sheet can be made to effectively exhibit the antiviral properties. Meanwhile, layers formed by printing or coating-fluid application may be disposed on the surface of the surface layer constituted of the antiviral poly(vinyl chloride)-based resin composition, so long as the antiviral properties are exhibited.

In the case of a multilayer structure, the layers to be superposed are not particularly limited. For example, use can be made of a layer constituted of the antiviral poly(vinyl chloride)-based resin composition, a poly(vinyl chloride)-based resin layer, and a layer of another thermoplastic resin. Furthermore, layers according to uses and required properties, such as any of various foamed resin layers, a design layer, e.g., a printed layer or a colored layer, and a base layer, e.g., woven fabric or nonwoven fabric, can be superposed. For the poly(vinyl chloride)-based resin layer, use can be made of either a single poly(vinyl chloride)-based resin, e.g., a suspension poly(vinyl chloride)-based resin or a poly(vinyl chloride)-based resin for paste, or a mixture of such resins.

The interior decorative sheet according to an embodiment of the invention can be suitable for use as a flooring material. For use as a flooring material, the interior decorative sheet is required to have durability, thickness, etc. It is hence preferable that the interior decorative sheet should be a layered product including a surface layer constituted of the antiviral poly(vinyl chloride)-based resin composition and a back layer. It is possible to ensure durability and thickness due to the back layer and to exhibit antiviral properties due to the surface layer.

The back layer of the flooring material preferably is a poly(vinyl chloride)-based resin layer, and it is possible to add 10-100 parts by weight of a plasticizer and 20-500 parts by weight of a filler to 100 parts by weight of the poly(vinyl chloride)-based resin(s). The poly(vinyl chloride) resins usable in the poly(vinyl chloride)-based resin layer in the back layer are not particularly limited, and use can be made of either any of a suspension poly(vinyl chloride)-based resin, a poly(vinyl chloride)-based resin for paste, and the like alone or a mixture of such resins.

The surface layer constituted of the antiviral poly(vinyl chloride)-based resin composition can be produced by a production process including a step in which a poly(vinyl chloride)-based resin for paste is mixed with a suspension poly(vinyl chloride)-based resin to obtain a poly(vinyl chloride)-based resin, a step in which the poly(vinyl chloride)-based resin is mixed with a plasticizer to obtain an antiviral poly(vinyl chloride)-based resin composition, and a step in which the antiviral poly(vinyl chloride)-based resin composition is melt-shaped.

It is preferable that the sulfonic-acid-based surfactant should have been added during the production of the poly(vinyl chloride)-based resin for paste. In this case, the surface layer can be produced by a production process including a step in which a poly(vinyl chloride)-based resin for paste that contains a sulfonic-acid-based surfactant is mixed with a suspension poly(vinyl chloride)-based resin to obtain a poly(vinyl chloride)-based resin, a step in which the poly(vinyl chloride)-based resin is mixed with a plasticizer to obtain an antiviral poly(vinyl chloride)-based resin composition, and a step in which the antiviral poly(vinyl chloride)-based resin composition is melt-shaped.

The step of obtaining a poly(vinyl chloride)-based resin and the step of obtaining an antiviral poly(vinyl chloride)-based resin composition may be successively conducted as separate steps, or may be simultaneously conducted. Use may be made of a method in which a plasticizer and other ingredient(s) are added to either a poly(vinyl chloride)-based resin for paste or a suspension poly(vinyl chloride)-based resin and, thereafter, the poly(vinyl chloride)-based resin for paste and the suspension poly(vinyl chloride)-based resin are mixed with each other.

Preferred from the standpoints of operation efficiency and cost is a production process wherein an antiviral poly(vinyl chloride)-based resin composition is obtained through a step in which a poly(vinyl chloride)-based resin for paste that contains a sulfonic-acid-based surfactant is mixed with a suspension poly(vinyl chloride)-based resin and in which a plasticizer, a stabilizer, etc. are added and kneaded.

For the step of obtaining a poly(vinyl chloride)-based resin, known production devices can be used. For example, the resin can be produced by evenly mixing a poly(vinyl chloride)-based resin for paste with a suspension poly(vinyl chloride)-based resin by means of a high-seed stirrer, low-speed stirrer, Henschel mixer, or the like. The poly(vinyl chloride)-based resin can be obtained also by subjecting the mixture obtained through the mixing to melt mixing by means of a batch kneading mixer, Banbury mixer, Kokneader, extruder, or the like. Furthermore, the mixture obtained through the melt mixing may be temporarily pelletized. It is also possible to use a poly(vinyl chloride)-based resin for paste to which a sulfonic-acid-based surfactant was added during the production of the poly(vinyl chloride)-based resin for paste.

For the step of obtaining an antiviral poly(vinyl chloride)-based resin composition, known production devices can be used. For example, the composition can be produced by evenly mixing a poly(vinyl chloride)-based resin for paste, a suspension poly(vinyl chloride)-based resin, a sulfonic-acid-based surfactant, and a plasticizer by means of a high-speed stirrer, low-speed stirrer, Henschel mixer, or the like. The antiviral poly(vinyl chloride)-based resin composition can be obtained also by subjecting the mixture obtained through the mixing to melt mixing by means of a batch kneading mixer, Banbury mixer, Kokneader, extruder, or the like. Furthermore, the mixture obtained through the melt mixing may be temporarily pelletized to obtain the antiviral poly(vinyl chloride)-based resin composition as pellets. Incidentally, additives such as a stabilizer and a filler can be added at will in accordance with intended uses. It is possible to use a poly(vinyl chloride)-based resin for paste to which a sulfonic-acid-based surfactant was added during the production of the poly(vinyl chloride)-based resin for paste.

The surface layer of the interior decorative sheet according to an embodiment of the invention can be obtained by melt-shaping the antiviral poly(vinyl chloride)-based resin composition. In cases when the interior decorative sheet has a single-layer structure, the surface layer constituted of the antiviral poly(vinyl chloride)-based resin composition is the interior decorative sheet. In cases when the interior decorative sheet has a multilayer structure, this interior decorative sheet is obtained by laminating the surface layer constituted of the antiviral poly(vinyl chloride)-based resin composition to other layer(s), e.g., a back layer. For laminating the surface layer to other layers, use can be made of production techniques such as hot laminating, hot pressing, bonding with an adhesive, etc.

For the step of melt-shaping the antiviral poly(vinyl chloride)-based resin composition, use can be made of a method of forming a sheet. Preferred as the sheet forming method is calendering or roll processing, from the standpoint of the thickness accuracy of the sheet obtained. From the standpoint of speed, calendering is preferred. Other general sheet forming methods can be used for forming the sheet. Examples thereof include extrusion molding and press molding.

In cases when a poly(vinyl chloride)-based resin for paste is mixed with a plasticizer, the resultant mixture frequently is pasty as stated above. For forming a pasty resin composition into a sheet, a coating machine such as, for example, a paste coater is generally used. In this case, there are limitations on the structure, thickness, and width of the sheet, production rate, etc., and this production method is not always suitable for sheet production. In view of this, the desired antiviral poly(vinyl chloride)-based resin sheet can be produced by using a blend of a poly(vinyl chloride)-based resin for paste with a suspension vinyl chloride resin and using an extruder or calendering machine, which has excellent sheet-forming properties.

[Third Aspect]

The interior decorative sheet made of a poly(vinyl chloride)-based resin according to the third aspect of the invention includes a base layer and an antiviral poly(vinyl chloride)-based resin layer, and the antiviral poly(vinyl chloride)-based resin layer has been disposed on the front surface side within the interior decorative sheet made of a poly(vinyl chloride)-based resin. The antiviral poly(vinyl chloride)-based resin layer includes a poly(vinyl chloride)-based resin for paste and a plasticizer.

A sulfonic-acid-based surfactant has been added beforehand to the poly(vinyl chloride)-based resin for paste to be used in the invention.

With respect to methods for the addition, one method is to add a sulfonic-acid-based surfactant as an emulsifying agent in the polymerization step described above. However, such addition of a sulfonic-acid-based surfactant may result in cases where a poly(vinyl chloride)-based resin for paste which has desired properties is not obtained due to the influence of the sulfonic-acid-based surfactant added.

Meanwhile, a sulfonic-acid-based surfactant can be added also in a post-polymerization step. It is noted that sulfonic-acid-based surfactants are water-soluble, and that in cases when a poly(vinyl chloride)-based resin for paste is produced by emulsion polymerization or seed emulsion polymerization, a latex including water as the medium is obtained as an intermediate form of the product of polymerization. Consequently, by adding a sulfonic-acid-based surfactant to this latex, the sulfonic-acid-based surfactant is satisfactorily dispersed into the poly(vinyl chloride)-based resin. By thus adding a sulfonic-acid-based surfactant to the latex resulting from polymerization, a poly(vinyl chloride)-based resin for paste which has desired properties is obtained while avoiding influences on the polymerization conditions.

Since a sulfonic-acid-based surfactant was added beforehand during the production of the poly(vinyl chloride)-based resin for paste, the sulfonic-acid-based surfactant in the poly(vinyl chloride)-based resin for paste is in a finely dispersed state. Because of this, the sulfonic-acid-based surfactant shows satisfactory dispersibility also in the poly(vinyl chloride)-based sol composition, making it possible to obtain the interior decorative sheet made of a poly(vinyl chloride)-based resin, without impairing the surface appearance.

The poly(vinyl chloride)-based resin to be used as the base of the poly(vinyl chloride)-based resin for paste to be used in the invention is not particularly limited. However, a poly(vinyl chloride)-based resin having a degree of polymerization of, for example, 600-5,000 is suitable.

As the sulfonic-acid-based surfactant to be used in the invention, the same sulfonic-acid-based surfactants as in the first aspect can be used. Preferred examples thereof are also the same.

The poly(vinyl chloride)-based resin for paste to be used in the invention must contain a sulfonic-acid-based surfactant in an amount of 0.1-7.5 parts by weight per 100 parts by weight of the resinous ingredient. The content thereof is preferably 0.5-5.0 parts weight, more preferably 1.0-2.5 parts by weight. In case where the content thereof is less than 0.1 part by weight, the interior decorative sheet has insufficient antiviral properties. In case where the content thereof exceeds 7.5 parts by weight, the antiviral poly(vinyl chloride)-based sol composition has poor defoamability. There is hence a possibility that the defoaming of the antiviral poly(vinyl chloride)-based sol composition might require much time or that the sol composition cannot be sufficiently defoamed and the interior decorative poly(vinyl chloride)-based resin sheet might have a surface with recesses and protrusions due to bubble inclusion, resulting in an impaired appearance. This trouble is explained below. In cases when an antiviral poly(vinyl chloride)-based sol composition is applied to a base layer and when bubbles remain in the antiviral poly(vinyl chloride)-based sol composition, then the antiviral poly(vinyl chloride)-based resin layer formed by the application also contains bubbles. Consequently, there are cases where in the antiviral poly(vinyl chloride)-based resin layer, some of the bubbles become protrusions and others break to leave the marks thereof in the surface, resulting in appearance failures. In addition, there are cases where the poor defoamability necessitates a separate defoaming step or where the defoaming step requires a prolonged time period to increase the production cost.

In the case where there is a possibility that the interior decorative sheet made of a poly(vinyl chloride)-based resin might come into contact with water, it is preferred to regulate the addition amount of the sulfonic-acid-based surfactant to 0.1-3.0 parts by weight, from the standpoint of preventing the interior decorative sheet made of a poly(vinyl chloride)-based resin from blushing. Especially in the case where the interior decorative sheet made of a poly(vinyl chloride)-based resin is transparent or has a dark color, the blushing is noticeable and it is hence more preferred to regulate the addition amount of the surfactant to 0.1-2.0 parts by weight.

The poly(vinyl chloride)-based resin for paste to be used in the invention may be constituted only of a poly(vinyl chloride)-based resin for paste which contains 0.1-7.5 parts by weight of a sulfonic-acid-based surfactant added thereto beforehand, or may be a mixture of such a surfactant-containing poly(vinyl chloride)-based resin for paste with other poly(vinyl chloride)-based resin(s) for paste. In the case where a plurality of poly(vinyl chloride)-based resins for paste are used as a mixture thereof, this mixture is not limited so long as a sulfonic-acid-based surfactant is contained therein in an amount of 0.1-7.5 parts by weight per 100 parts by weight of the resinous ingredient of the whole mixture.

As the plasticizer, a common plasticizer can be used. Examples thereof include di-2-ethylhexyl phthalate (DOP), dibutyl phthalate (DBP), diisononyl phthalate (DINP), diisodecyl phthalate (DIDP), diundecyl phthalate (DUP), di-2-ethylhexyl adipate (DOA), diisodecyl adipate (DIDA), di-2-ethylhexyl sebacate (DOS), tricresyl phosphate (TCP), trixylenyl phosphate (TXP), trioctyl trimellitate (TOTM), acetyl tributyl citrate (ATBC), polyester-based plasticizers, and chlorinated paraffins. One plasticizer may be used alone, or plasticizers of multiple kinds may be used in combination.

The amount of the plasticizer to be added is 10-100 parts by weight per 100 parts by weight of the poly(vinyl chloride)-based resin for paste. In case where the addition amount of the plasticizer exceeds 100 parts by weight, fouling substances are prone to adhere to the resultant interior decorative sheet made of a poly(vinyl chloride)-based resin and the adherent fouling substances cannot be removed by simple cleaning. In case where the addition amount thereof is less than 10 parts by weight, the antiviral poly(vinyl chloride)-based sol composition is difficult to prepare or apply. From the standpoint of obtaining an antiviral poly(vinyl chloride)-based sol composition which is easy to prepare and apply and which has high antifouling properties, the addition amount of the plasticizer is preferably 10-82 parts by weight, more preferably 10-40 parts by weight.

Other compounding agents generally added to resins may be added according to need, such as stabilizers, fillers, ultraviolet absorbers, light stabilizers, ultraviolet-screening agents, antistatic agents, foaming agents, flame retardants, thickeners, surfactants, fluorescent agents, crosslinking agents, impact modifiers, antibacterial agents, viscosity-lowering agents, fungicides, flame retardants, flameproofing agents, and defoamers.

The base layer is not particularly limited. Use can be made of a sheet obtained by forming a synthetic resin, e.g., a vinyl chloride resin, into a sheet using a calendering machine, extrusion molding machine, injection molding machine, compression molding machine, casting machine, or the like, or of a material such as paper, woven fabric, or nonwoven fabric. A layer of a material such as paper, woven fabric, or nonwoven fabric may be laminated to a layer of a synthetic resin to obtain a base layer.

The interior decorative poly(vinyl chloride)-based resin sheet of the invention is obtained by applying the antiviral poly(vinyl chloride)-based sol composition of the invention to a surface of a base layer.

The antiviral poly(vinyl chloride)-based sol composition is obtained from a poly(vinyl chloride)-based resin for paste to which a sulfonic-acid-based surfactant has been added beforehand, by stirring this poly(vinyl chloride)-based resin for paste together with a plasticizer, etc. by means of a mixer or the like.

After being applied, the antiviral poly(vinyl chloride)-based sol composition must be solidified by drying. Examples of conditions of the solidification by drying include a method in which the sol composition applied is heated at a temperature of 180-220° C. for 3-5 minutes using an oven or the like.

For stirring the poly(vinyl chloride)-based resin for paste together with a plasticizer, use can be made of a dissolver type mixer, butterfly mixer, universal stirrer, or the like.

For applying the antiviral poly(vinyl chloride)-based sol composition to a base layer, use can be made of knife coating, gravure coating, roll coating, bar coating, die coating, or the like.

For drying and solidifying the antiviral poly(vinyl chloride)-based sol composition after the application, use can be made of a hot-air drying oven, far-infrared-radiation drying oven, or the like.

Furthermore, the interior decorative sheet may be produced so as to have a multilayer structure by disposing any of various foamed resin layers and a design layer such as a printed layer or a colored layer on a base and further disposing an antiviral poly(vinyl chloride)-based resin layer by applying the antiviral poly(vinyl chloride)-based sol composition thereon. Layers can be superposed in accordance with intended uses and required properties. In either case, however, it is necessary that the base should have strength which enables the base to withstand high temperatures during the heating. In the case where the antiviral poly(vinyl chloride)-based sol composition is applied to the design layer, it is preferable that the antiviral poly(vinyl chloride)-based resin layer should be transparent. Thus, the design layer can be seen through the surface, and the interior decorative sheet has excellent design attractiveness. Besides being a printed layer or colored layer mentioned above as an example, the design layer may be any layer which visually presents a beautiful appearance. It is also possible to configure a design layer, e.g., a colored layer or a printed layer, as an antiviral poly(vinyl chloride)-based resin layer.

A grain can be formed in the upper surface of the surface layer of the interior decorative poly(vinyl chloride)-based resin sheet by embossing or the like. The formation of a grain can widen design variations.

A preferred form of fine recesses and protrusions to be formed in the upper surface of the surface layer of the interior decorative sheet made of a poly(vinyl chloride)-based resin has an arithmetic average roughness Ra of 5-20 µm, more preferably 10-15 µm. A pattern made up of continuous gentle-sloping (broad) recesses and protrusions which form delicate and complicated curves is preferable to a pattern in which independent (sharp) protrusions are scatteringly present, from the standpoint of antifouling property.

A topcoat layer may be disposed on a surface of the interior decorative poly(vinyl chloride)-based resin sheet of the invention unless the antiviral properties are lessened thereby. By disposing a topcoat layer, the antifouling properties can be improved. The topcoat layer can be disposed, for example, by applying a coating material prepared from a resin composition for topcoating. As the resin of the resin composition for topcoating, use can be made of an acrylic resin, urethane resin, fluororesin, or the like.

In the case of disposing a topcoat layer by applying a coating agent (coating material), the coating agent is applied to the surface of the antiviral poly(vinyl chloride)-based resin layer so that the topcoat layer has fine interstices therein. Consequently, the sulfonic-acid-based surfactant contained in the antiviral poly(vinyl chloride)-based resin layer can be partly exposed in the surface and, hence, is capable of attacking viruses which have come into contact with the surface of the interior decorative sheet. Thus, even when a topcoat layer has been disposed, the interior decorative sheet exhibits the antiviral properties.

The interior decorative poly(vinyl chloride)-based resin sheet of the invention is effective, for example, against viruses having an envelope.

Examples of the viruses having an envelope include influenza viruses such as avian influenza viruses, human influenza viruses, and porcine influenza viruses, hepatitis B virus, hepatitis C virus, human immunodeficiency virus, varicella-zoster virus, herpes simplex virus, human herpes virus, mumps virus, and RS virus.

[Fourth Aspect]

The fourth aspect of the invention is described below in detail.

The interior decorative sheet according to the fourth aspect of the invention is an interior decorative sheet including a surface layer which is constituted of a poly(vinyl chloride)-based resin composition including 100 parts by weight of a poly(vinyl chloride)-based resin, 0.1-10.0 parts by weight of a sulfonic-acid-based surfactant, 10-50 parts by weight of a plasticizer, and 1-20 parts by weight of a silicone-based copolymer.

From the standpoint of imparting antiviral properties to the interior decorative sheet, a sulfonic-acid-based surfactant must be contained in an amount of 0.1-10.0 parts by weight per 100 parts by weight of the poly(vinyl chloride)-based resin.

This feature is first described below in detail.

The poly(vinyl chloride)-based resin to be used in the surface layer of the interior decorative sheet is a thermoplastic resin which includes vinyl chloride as the main constituent unit and which may contain comonomer units other than vinyl chloride. The content of such comonomer units other than vinyl chloride is not particularly limited so long as the present invention is not affected thereby. However, the content of the comonomer units in all the monomer units is preferably 0-30% by mole, more preferably 0-10% by mole. Examples thereof include poly(vinyl chloride), ethylene/vinyl chloride copolymers, propylene/vinyl chloride copolymers, vinyl chloride/acrylic resin copolymers, vinyl chloride/urethane copolymers, vinyl chloride/vinylidene chloride copolymers, and vinyl chloride/vinyl acetate copolymers. One of these poly(vinyl chloride)-based resins may be used alone, or two or more thereof may be used in combination. Poly(vinyl chloride) is preferred of these poly(vinyl chloride)-based resins from the standpoints of processability and cost.

The average degree of polymerization of the poly(vinyl chloride)-based resin is not particularly limited so long as forming is substantially possible. However, the average degree of polymerization thereof is preferably in the range of 500-2,000, more preferably in the range of 700-1,800. In case where the average degree of polymerization thereof is less than 500, the composition is difficult to process since the melt viscosity thereof is low. In case where the average degree of polymerization thereof exceeds 2,000, there is a possibility that the composition might be difficult to process because of the high melt viscosity thereof. With respect to the antifouling properties of the interior decorative sheet, there is a tendency that the higher the average degree of polymerization of the poly(vinyl chloride)-based resin, the higher the antifouling properties.

Examples of the sulfonic-acid-based surfactant include surfactants based on an alkylsulfuric acid ester, surfactants based on an alkylbenzenesulfonic acid, surfactants based on an alkylnaphthalenesulfonic acid, surfactants based on an (alkyldiphenyl ether)disulfonic acid, surfactants based on a polyoxyethylene alkylsulfuric acid ester, and naphthalenesulfonic acid/formalin condensates. Surfactants based on an alkylbenzenesulfonic acid are preferred because these surfactants have a high antiviral effect. More preferred are surfactants based on dodecylbenzenesulfonic acid. Furthermore, suitable for use as the sulfonic-acid-based surfactant are alkali metal salts, such as sodium salts and potassium salts, and salts with alkaline earth metals such as calcium and barium.

The content of the sulfonic-acid-based surfactant used in the invention is 0.1-10.0 parts by weight per 100 parts by weight of the poly(vinyl chloride)-based resin, and is preferably 1-8.1 part by weight, more preferably 1-5 parts by weight. In case where the content thereof is less than 0.1 part by weight, the antiviral effect is insufficient. In case where the content thereof exceeds 10 parts by weight, there is a possibility that this composition might have poor processability to give an antiviral decorative sheet which has a poor surface state due to bleeding and is apt to be fouled.

There are cases where a poly(vinyl chloride)-based resin takes a color when formed after addition of a sulfonic-acid-based surfactant thereto.

With respect to this problem, the coloring of the resin can be effectively inhibited by using a vinyl-chloride-based resin for paste into which a sulfonic-acid-based surfactant has been added beforehand.

It is noted that the antiviral vinyl-chloride-based resin composition exhibits antiviral properties since a sulfonic-acid-based surfactant has been added in a given amount to the poly(vinyl chloride)-based resin. From the standpoint of enabling the composition to exhibit higher antiviral properties and to be inhibited from suffering initial discoloration during forming, it is preferable that the sulfonic-acid-based surfactant should have been added to a vinyl-chloride-based resin for paste. In this connection, it is possible to add a sulfonic-acid-based surfactant as, for example, an emulsifying agent during polymerization. Such addition of a sulfonic-acid-based surfactant may result in cases where a vinyl-chloride-based resin for paste which has desired properties is not obtained due to the influence of the sulfonic-acid-based surfactant added.

Meanwhile, it is noted that sulfonic-acid-based surfactants are water-soluble, and that in cases when a vinyl chloride resin for paste is produced by emulsion polymerization or seed emulsion polymerization, a latex including water as the medium is obtained as an intermediate form of the product of polymerization. Consequently, by adding a sulfonic-acid-based surfactant to this latex, the sulfonic-acid-based surfactant is satisfactorily dispersed into the vinyl chloride resin. By thus adding a sulfonic-acid-based surfactant to the latex resulting from polymerization, a vinyl chloride resin for paste which has desired properties is obtained while avoiding influences on the polymerization conditions. Thus, the effect of attaining both high antiviral properties and inhibition of initial discoloration during forming can be more efficiently obtained.

As the sulfonic-acid-based surfactant to be added to the latex resulting from polymerization when producing a vinyl-chloride-based resin for paste, use can be made of the sulfonic-acid-based surfactant described above. Examples thereof include surfactants based on an alkylsulfuric acid ester, surfactants based on an alkylbenzenesulfonic acid, surfactants based on an alkylnaphthalenesulfonic acid, surfactants based on an (alkyldiphenyl ether)disulfonic acid, surfactants based on a polyoxyethylene alkylsulfuric acid ester, and naphthalenesulfonic acid/formalin condensates. Surfactants based on an alkylbenzenesulfonic acid are preferred because these surfactants have a high antiviral effect. More preferred are surfactants based on dodecylbenzenesulfonic acid. Furthermore, suitable for use as the sulfonic-acid-based surfactant are alkali metal salts, such as sodium salts and potassium salts, and salts with alkaline earth metals such as calcium and barium.

The content of the sulfonic-acid-based surfactant in the poly(vinyl chloride)-based resin for paste into which the sulfonic-acid-based surfactant has been added beforehand is preferably 0.1-15% by weight, more preferably 0.7-10% by weight, especially preferably 1.0-7.5% by weight, based on the sum of the poly(vinyl chloride)-based resin for paste and the sulfonic-acid-based surfactant. In case where the content thereof is less than 0.1% by weight, the interior decorative sheet obtained has poor antiviral properties. In case where the content thereof exceeds 15% by weight, the efficiency of the production of this vinyl-chloride-based resin for paste becomes poor.

The average degree of polymerization of the poly(vinyl chloride)-based resin for paste is not particularly limited so long as forming is substantially possible. However, the average degree of polymerization thereof is preferably in the range of 500-2,000, more preferably in the range of 700-1,800. In case where the average degree of polymerization thereof is less than 500, the composition is difficult to process since the melt viscosity thereof is low. In case where the average degree of polymerization thereof exceeds 2,000, there is a possibility that the composition might be difficult to process because of the high melt viscosity thereof.

In cases when a poly(vinyl chloride)-based resin for paste is used, processing methods are limited to coating and the like since the poly(vinyl chloride)-based resin for paste has the property of becoming pasty at ordinary temperature when mixed with a liquid such as a plasticizer. In the case where the resin composition is to be formed by a melt shaping method in which the resin composition is thermally melted, kneaded, shaped, and then solidified by cooling, it is preferred to blend the resin with a suspension vinyl-chloride-based resin.

The term "suspension vinyl-chloride-based resin" means a vinyl-chloride-based resin obtained mainly by a suspension polymerization method and having a porous indefinite shape with a particle diameter of 50-200 μm. Due to the porous shape, this vinyl-chloride-based resin can absorb liquids such as plasticizers and can hence prevent the composition from becoming pasty.

The blending ratio between the vinyl-chloride-based resin for paste and the suspension vinyl-chloride-based resin is not particularly limited so long as the sulfonic-acid-based surfactant is contained in an amount of 0.1-10.0 pasts by weight per 100 parts by weight of the poly(vinyl chloride)-based resin (here, the sum of the vinyl-chloride-based resin for paste and the suspension vinyl-chloride-based resin) and so long as the composition can be formed without arousing a problem. However, the amounts of the vinyl-chloride-based resin for paste and the suspension vinyl-chloride-based resin in the poly(vinyl chloride)-based resin are preferably 100-1 part by weight and 0-99 parts by weight, respectively. More preferably, the amounts of the vinyl-chloride-based resin for paste and the suspension vinyl-chloride-based resin are 70-10 parts by weight and 30-90 parts by weight, respectively. Most preferably, the amounts of the vinyl-chloride-based resin for paste and the suspension vinyl-chloride-based resin are 50-20 parts by weight and 50-80 parts by weight, respectively.

The average degree of polymerization of the suspension poly(vinyl chloride)-based resin is not particularly limited so long as forming is substantially possible. However, the average degree of polymerization thereof is preferably in the range of 500-2,000, more preferably in the range of 700-1,800. In case where the average degree of polymerization thereof is less than 500, the composition is difficult to process since the melt viscosity thereof is low. In case where the average degree of polymerization thereof exceeds 2,000, there is a possibility that the composition might be difficult to process because of the high melt viscosity thereof.

Next, from the standpoint of imparting antifouling properties to the interior decorative sheet, the composition must contain 1-20 parts by weight of a silicone-based copolymer and 10-50 parts by weight of a plasticizer per 100 parts by weight of the poly(vinyl chloride)-based resin.

This feature is described below in detail.

The silicone-based copolymer may be a copolymer of a silicone with any of various organic resins copolymerizable with silicones. Examples of the silicone-copolymerizable resins include acrylic resins, urethane resins, epoxy resins, polyester resins, fluororesins, polyimide resins, and polycarbonate resins. By reacting a silicone with one or more of these copolymerizable resins, a silicone-based copolymer is obtained. A silicone-based copolymer obtained by reacting a silicone with any of acrylic resins, urethane resins, epoxy resins, and polyester resins, among those, is preferred since this silicone-based copolymer has satisfactory compatibility with vinyl-chloride-based resins.

Examples of the structure of the silicone-based copolymer include: a block copolymer in which one or more silicone chains have been block-wise disposed in a framework of a silicone-copolymerizable resin; and a graft copolymer in which one or more silicone chains have been disposed as side chains of a silicone-copolymerizable resin or one or more chains of a silicone-copolymerizable resin have been disposed as side chains of a silicone. Preferred are the graft copolymers. More preferred are the graft copolymer in which one or more chains of a copolymerizable resin have been disposed as side chains of a silicone.

As a silicone-based graft copolymer, use can be made of a copolymer of a core/shell structure which is configured of a silicone-based composite rubber and a graft layer disposed on the periphery thereof. Examples thereof include a graft copolymer based on a silicone/acrylic composite rubber. The graft copolymer based on a silicone/acrylic composite rubber is a copolymer obtained by grafting a vinyl-based polymer, e.g., a polymer of a methacrylic ester or acrylic ester, onto the periphery of a particulate composite rubber configured of a polyorganosiloxane and a poly(alkyl (meth)acrylate).

The addition amount of the silicone-based copolymer is 1-20 parts by weight per 100 parts by weight of the vinyl-chloride-based resin. This resin composition can be processed by a common sheet forming method such as calendering or extrusion molding. However, in case where the addition amount of the silicone-based copolymer exceeds 20 parts by weight, the composition has reduced processability and the sheet formed therefrom has appearance failures. In case where the addition amount thereof is less than 1 part by weight, troubles arise, such as insufficient antifouling properties. From the standpoint of enabling the interior decorative sheet to have a satisfactory appearance and satisfactory antifouling properties, the addition amount is preferably 1-20 parts by weight, more preferably 3-10 parts by weight.

As the plasticizer, a common plasticizer can be used. Examples thereof include plasticizers based on esters of aliphatic dibasic acids, such as phthalic-ester-based plasticizers, e.g., DOP (di-2-ethylhexyl phthalate), DINP (diisononyl phthalate), and DIDP (diisodecyl phthalate), adipic-ester-based plasticizers, e.g., DOA (di-2-ethylhexyl adipate) and DIDA (diisodecyl adipate), sebacic-ester-based plasticizers, e.g., DOS (di-2-ethylhexyl sebacate), azelaic-ester-based plasticizers, e.g., DOZ (di-2-ethylhexyl azelate), phosphoric-ester-based plasticizers such as TCP (tricresyl phosphate), TPP (triphenyl phosphate), and TXP (trixylenyl phosphate), trimellitic-ester-based plasticizers such as TOTM (tris-2-ethylhexyl trimellitate), polyester-based plasticizers, epoxy-based plasticizers, and sulfonic-ester-based plasticizers. Examples of plasticizers having satisfactory compatibility with vinyl-chloride-based resins include phthalic-ester-based plasticizers and polyester-based plasticizers having a high molecular weight. One plasticizer may be used alone, or plasticizers of multiple kinds may be used in combination.

The addition amount of the plasticizer is 10-50 parts by weight per 100 parts by weight of the vinyl-chloride-based resin. In case where the addition amount of the plasticizer exceeds 50 parts by weight, fouling substances are prone to adhere to the interior decorative sheet obtained from this composition and the adherent fouling substances cannot be removed by simple cleaning. Namely, sufficient antifouling properties are not obtained. In case where the addition amount thereof is less than 10 parts by weight, this composition is difficult to process or can be processed to only give an interior decorative sheet which is so rigid that application thereof arouses troubles such as cracking and blushing. The addition amount of the plasticizer is preferably 10-40 parts by weight, more preferably 20-40 parts by weight.

A filler can be added to the interior decorative sheet for the purpose of improving the processability. As the filler, use can be made of calcium carbonate, silica, and other inorganic fillers such as platy fillers, e.g., talc and mica, clays, e.g., bentonite and calcined kaolin, metal oxides, e.g., magnesium oxide and alumina, and metal hydroxides, e.g., magnesium hydroxide and aluminum hydroxide. Any of various surface treatments with fatty acids, modified fatty acids, etc. may have been given to the filler in order to enhance the affinity for the vinyl-chloride-based resin.

It is preferable that the amount of the filler to be added should be 1-50 parts by weight per 100 parts by weight of the vinyl-chloride-based resin. In case where the addition amount of the filler exceeds 50 parts by weight, the filler exerts a greater influence on the surface smoothness of the interior decorative sheet and enhances the surface roughness of the surface layer, thereby rendering fouling substances prone to adhere to the surface. When the addition amount thereof is less than 1 part by weight, there are cases where the effect of improving processability is not obtained. The addition amount of the filler is preferably 5-30 parts by weight, more preferably 10-20 parts by weight. In the case of disposing a design layer such as a printed layer beneath the surface layer, it is preferable that the addition amount of the filler should be 10 parts by weight or less since the surface layer is required to have transparency for enabling the design to be seen.

The antifouling properties of the surface layer of the interior decorative sheet vary depending on the particle size and shape of the filler added. With respect to the average particle diameter of the filler, when the average particle diameter is expressed in terms of median diameter which is the 50% diameter calculated from a cumulative particle size distribution determined by laser diffractometry, a filler having a median diameter in the range of 2-10 μm is preferred. When the average particle diameter is expressed in terms of specific-surface-area diameter which is an average particle diameter calculated by conversion from a specific surface area determined by the BET method, Blaine permeation method, or the like, a filler having a specific-surface-area diameter in the range of 1-5 μm is preferred. With respect to the shape of the filler, a platy shape is preferred. In cases when a filler-containing resin compound is processed, a platy filler is more apt to be aligned along the direction of the flow of the resin compound being processed, as compared with spherical fillers or fillers of indefinite shapes, and are apt to be present in the aligned state also in the sheet formed. Consequently, the resultant sheet tends to have reduced surface roughness, and fouling substances are less apt to adhere thereto and are easy to remove therefrom. Examples of the platy filler include talc and mica.

It is preferred to add an acrylic polymeric processing aid to the interior decorative sheet for the purpose of improving the processability. Examples of the acrylic polymeric processing aid include acrylic polymeric processing aids such as methyl methacrylate/alkyl acrylate copolymers, e.g., methyl methacrylate/butyl acrylate copolymers.

By adding an acrylic polymeric processing aid, the rotational flow and degassing within the bank during forming by roll processing or calendering are rendered satisfactory and plate-out is inhibited. Consequently, a sheet having a satisfactory appearance is obtained.

It is preferred to add a β-diketone or a coloring inhibitor constituted of a combination of an anion of an inorganic compound containing any of elements belonging to Groups 13, 15, and 17 of the periodic table (e.g., $PF_6^-$, $SbF_6^-$, $AsF_6^-$, $ClO_4^-$, or $BF_4^-$) with a cation of any of elements belonging to Groups 1, 2, and 12 of the periodic table (e.g., $Na^+$, $Li^+$, $Mg^{2+}$, $Ca^{2+}$ or $Zn^{2+}$), to the interior decorative sheet in order to further prevent the coloring during processing. Especially preferred of these are sodium-perchlorate-based coloring inhibitors. The amount of the coloring inhibitor to be added is preferably 0.1-1 part by weight per 100 parts by weight of the vinyl-chloride-based resin.

Other compounding agents generally added to resins may be added according to need, such as stabilizers, antioxidants, ultraviolet absorbers, light stabilizers, ultraviolet-screening agents, antistatic agents, flame retardants, thickeners, surfactants, fluorescent agents, crosslinking agents, and impact modifiers.

In the case where preliminary kneading is necessary for obtaining the interior decorative sheet, known devices in common use for thermoplastic resins can be utilized. For example, use may be made of a method in which the composition of the invention is evenly mixed by means of a high-speed stirrer, low-speed stirrer, Henschel mixer, or the like, subsequently melt-mixed by means of a batch kneading mixer, Banbury mixer, Kokneader, extruder, or the like, and immediately formed. The composition which has undergone melt mixing may be temporarily pelletized and thereafter formed.

The interior decorative sheet can be formed by a common sheet forming method. Examples thereof include melt shaping methods, such as roll processing, calendering, extrusion molding, and press molding, and coating techniques. From the standpoints of speed and the thickness accuracy of the sheet obtained, melt shaping methods are preferred. Of these, calendering is preferred.

Recesses and protrusions (grain) can be formed in the upper surface of the surface layer of the interior decorative sheet by embossing or the like. The formation of recesses and protrusions (grain) can widen design variations, and an improvement in antiviral properties can be expected depending on the shape of the recesses and protrusions (grain).

A preferred form of fine recesses and protrusions to be formed in the upper surface of the surface layer of the interior decorative sheet has an arithmetic average roughness Ra of 5-20 μm, more preferably 10-15 μm. A pattern made up of continuous gentle-sloping (broad) recesses and protrusions which form delicate and complicated curves is preferable to a pattern in which independent (sharp) protrusions are scatteringly present, from the standpoints of antiviral property and antifouling property.

The interior decorative sheet at least includes the surface layer constituting an outermost surface, and may be constituted of a single layer or have a multilayer structure composed of a plurality of layers. In the case of a multilayer structure, the layers to be superposed are not particularly limited. A poly(vinyl chloride)-based resin layer similar to the surface layer, a layer of another thermoplastic resin, any of various foamed resin layers, a design layer such as a printed layer or colored layer, a base layer such as woven fabric or nonwoven fabric, and the like can be superposed in accordance with intended uses and required properties.

[Fifth Aspect]

It is essential that the antiviral wallpaper according to the fifth aspect of the invention should include a resin layer and a base layer, the resin layer including a resinous ingredient that includes a poly(vinyl chloride) resin for paste into which a sulfonic-acid-based surfactant has been incorporated beforehand, specifically, a vinyl chloride resin for paste which contains a sulfonic-acid-based surfactant in an amount of 1.2% by mass or larger based on the sum of the poly(vinyl chloride) resin for paste and the sulfonic-acid-based surfactant. Among steps for producing a wallpaper is a step in which a vinyl chloride for paste is mixed with a plasticizer, filler, stabilizer, foaming agent, etc. to produce a sol. However, since sulfonic-acid-based surfactants are insoluble in plasticizers, addition of a sulfonic-acid-based surfactant during this step arouses a problem in that the sulfonic-acid-based surfactant shows poor dispersibility in the sol to impair the beautiful appearance of the product by causing appearance failures such as streaks.

Meanwhile, it is noted that sulfonic-acid-based surfactants are water-soluble, and that in cases when a vinyl chloride resin for paste is produced by emulsion polymerization or seed emulsion polymerization, a latex including water as the medium is obtained as an intermediate form of the product of polymerization. Consequently, by adding a sulfonic-acid-based surfactant to this latex, the sulfonic-acid-based surfactant is satisfactorily dispersed into the vinyl chloride resin. By thus adding a sulfonic-acid-based surfactant to the latex resulting from polymerization, a poly(vinyl chloride) resin for paste which has desired properties is obtained while avoiding influences on the polymerization conditions. By using the vinyl chloride resin for paste obtained by the method, into which a sulfonic-acid-based surfactant has been incorporated beforehand, a wallpaper can be obtained without impairing the beautiful appearance.

The vinyl chloride resin to be used as the base of the vinyl chloride resin for paste to be used in the invention is not particularly limited. However, a vinyl chloride resin having a degree of polymerization of, for example, 600-3,000 is suitable.

As the sulfonic-acid-based surfactant to be used in the invention, the same sulfonic-acid-based surfactants as in the first aspect can be used. Preferred examples thereof are also the same.

The resinous ingredient to be used in the invention must contain a sulfonic-acid-based surfactant in an amount of 1.2% by weight or larger based on the sum of the poly(vinyl chloride) resin for paste and the sulfonic-acid-based surfactant. The content of the sulfonic-acid-based surfactant is preferably 1.5-49.9% by weight, more preferably 2-20% by weight. In case where the content thereof is less than 1.2% by weight, the antiviral properties are not stably exhibited. In cases when the resinous ingredient contains a sulfonic-acid-based surfactant in an amount of 1.5% by weight or larger, more stable antiviral properties are exhibited. By regulating the content thereof to 2.0% by weight or above, higher antiviral properties are obtained. In cases when the content thereof is 20% by weight of less, the composition is excellent in terms of having more stable processability.

As the vinyl chloride resin for paste to be used in the invention, the vinyl chloride resin for paste into which a sulfonic-acid-based surfactant has been incorporated beforehand in an amount of 1.2% by weight or larger may be used alone. Alternatively, this vinyl chloride resin for paste may be mixed with another vinyl chloride resin to give a mixture for use as the resinous ingredient. In either case, however, the resinous ingredient must contain a sulfonic-acid-based surfactant in an amount of 1.2% by weight or larger based on the resinous ingredient, i.e., the total amount of all the vinyl chloride resin(s). The content of the sulfonic-acid-based surfactant is preferably 1.5-49.9% by weight, more preferably 2-20% by weight. In case where the content thereof is less than 1.2% by weight, the antiviral properties are not stably exhibited.

According to need, a foaming agent may be used for the antiviral wallpaper of the invention. In this case, however, it is preferred to regulate the addition amount thereof to 0.01-5 parts by weight, preferably 0.1-4 parts by weight, more preferably 0.5-3 parts by weight, per 100 parts by weight of the resinous ingredient. By regulating the addition amount of the foaming agent to 0.1 part by weight or larger per 100 parts by weight of the resinous ingredient, a wallpaper having a higher expansion ratio can be obtained. By regulating the addition amount thereof to 0.5 parts by weight or larger, the expansion ratio can be further heightened. Meanwhile, it has been ascertained that in the antiviral wallpaper of the invention, the sulfonic-acid-based surfactant is present between segments of the vinyl chloride resin and the regions occupied by the sulfonic-acid-based surfactant enlarges as the content thereof increases. The sulfonic-acid-based surfactant in this state reduces the adhesion of the vinyl chloride resin segments to each other to cause a decrease in elastic modulus. In case where a decrease in elastic modulus occurs, it becomes difficult to retain the cells formed by the decomposition of the foaming agent and the cells can contract. So long as the addition amount of the foaming agent is 5 parts by weight or less per 100 parts by weight of the resinous ingredient, the influence which causes the cells to contract is substantially nil or only slight and the beautiful appearance of the wallpaper is not impaired. However, when the addition amount thereof exceeds 5 parts by weight, there are cases where the contraction of the cells is enhanced and appearance failures, e.g., discoloration, occur.

In one of preferred embodiments of the invention, substantially no foaming agent is incorporated for the purpose of enabling the antiviral wallpaper of the invention to have required properties including smoothness and strength.

As the foaming agent for use in the invention, a known foaming agent can be employed. Examples thereof include azodicarbonamide (ADCA), azobisformamide, hydroxybenzenesulfonylhydrazide, and p-toluenesulfonylhydrazide.

A topcoat layer may be disposed on a surface of the antiviral wallpaper of the invention unless the antiviral properties are lessened thereby. The topcoat layer can be disposed, for example, by applying a coating material prepared from a resin composition for topcoating. As the resin for topcoating, use can be made of an acrylic resin, urethane resin, fluororesin, or the like. In cases when the topcoating can reduce the coefficient of dynamic friction of the surface of the wallpaper, the wallpaper can be made to be in the fourth or higher grade in a test according to a regulation for the performance of surface-reinforced wallpapers. In this case, it is preferred to regulate the coefficient of dynamic friction, as determined through a test according to, for example, ASTM D 1894, to 0.5 or less.

The regulation for the performance of surface-reinforced wallpapers is a regulation made by Wallcoveing Wholesalers Conference and Wallcoverigs Association with respect to the quality of surface-reinforced wallpapers, a test method therefor, etc. Specifically, in the test method, a wallpaper is subjected to a scratch test and the scratch resistance is assessed by visually examining the resultant surface. The scratch resistance is assessed in five grades; wallpapers rated as in the fourth or higher grade are recognized as surface-reinforced wallpapers.

In the case of disposing a topcoat layer by applying a coating agent, the coating agent is applied to the resin layer so that the topcoat layer has fine interstices therein. Consequently, the sulfonic-acid-based surfactant contained in the resin layer can be partly exposed in the surface and, hence, is capable of attacking viruses which have come into contact with the surface of the wallpaper. Thus, even when a topcoat layer has been disposed, the wallpaper exhibits the antiviral properties.

The antiviral wallpaper of the invention is effective, for example, against viruses having an envelope. Examples of the viruses having an envelope include influenza viruses such as avian influenza viruses, human influenza viruses, and porcine influenza viruses, hepatitis B virus, hepatitis C virus, human immunodeficiency virus, varicella-zoster virus, herpes simplex virus, human herpes virus, mumps virus, and RS virus.

A process for producing the antiviral wallpaper of the invention is characterized by producing the wallpaper through: a step in which a vinyl chloride resin for paste into which a sulfonic-acid-based surfactant has been incorporated beforehand in an amount of 1.2% by weight or larger is used to obtain a vinyl chloride resin paste sol; and a step in which the vinyl chloride resin paste sol is applied to a base. Specific examples thereof include a production process in which a vinyl chloride resin for paste into which a sulfonic-acid-based surfactant has been incorporated beforehand in an amount of 1.2 parts by weight or larger is stirred together with a plasticizer, stabilizer, foaming agent, filler, etc. to produce a paste sol and this paste sol is applied to backing paper and then solidified by drying. For the stirring and application, known methods can be used. Various additives such as a colorant, processing aid, antibacterial agent, fungicide, flame retardant, flameproofing agent, and defoamer may be suitably added to the paste sol composition unless the antiviral properties are lessened thereby.

The plasticizer is not particularly limited. Examples thereof include di-2-ethylhexyl phthalate (DOP), diisononyl phthalate, dibutyl phthalate, dihexyl phthalate, diisodecyl phthalate, butyl benzyl phthalate, trioctyl phthalate, dioctyl adipate, chlorinated fatty acid esters, chlorinated paraffins, epoxidized soybean oil, and epoxidized fatty acid esters. Two or more of these may be used in combination.

The stabilizer is not particularly limited. Examples thereof include barium (Ba)-based stabilizers, calcium-based stabilizers, tin-based stabilizers, zinc (Zn)-based stabilizers, and potassium-based stabilizers. Two or more of these may be used in combination.

The filler is not particularly limited. Examples thereof include calcium carbonate, magnesium carbonate, titanium oxide, magnesium silicate, and diatomaceous earth. Two or more of these may be used in combination.

The backing paper to be used as a base layer in the antiviral wallpaper of the invention is not particularly limited. Examples thereof include plain pulp paper, flameproof pulp paper, calcium carbonate paper, aluminum hydroxide paper, and fleece paper.

In the antiviral wallpaper of the invention, a printed layer may be disposed on the base layer unless the antiviral properties are lessened thereby. For disposing the printed layer, a known method can be used. Examples thereof include gravure printing, flexographic printing, offset printing, and silk screen printing. Any of various surface-treating agents may be further used for the purpose of improving the applicability and adhesion of the printed layer or reducing gloss. In the case where the topcoat layer is to be disposed besides the printed layer, it is preferred to dispose the topcoat layer over the printed layer.

EXAMPLES

The present invention will be explained below in detail by reference to Examples, but the invention should not be construed as being limited to the following Examples.
[First Aspect]

The compounding agents used in the Examples and the Comparative Examples are the following substances.

Vinyl-chloride-based resin 10A-1: suspension vinyl-chloride-based resin; average degree of polymerization, 1,000

Vinyl-chloride-based resin 10A-2: suspension vinyl-chloride-based resin; average degree of polymerization, 700

Vinyl-chloride-based resin 10B-1: vinyl-chloride-based resin for paste; average degree of polymerization, 850 (content of sodium dodecylbenzenesulfonate, 5.0 wt %)

Vinyl-chloride-based resin 10B-2: vinyl-chloride-based resin for paste; average degree of polymerization, 850 (content of sodium dodecylbenzenesulfonate, 7.5 wt %)

Vinyl-chloride-based resin 10B-3: vinyl-chloride-based resin for paste; average degree of polymerization, 850 (containing no sodium dodecylbenzenesulfonate)

Plasticizer 10C-1: di-2-ethylhexyl phthalate

Stabilizer 10D-1: metal soap

Additive 10E-1: sodium dodecylbenzenesulfonate

<Formation Conditions 101>

Each of the mixtures of Examples and Comparative Examples shown in Tables 101 and 103 was kneaded for 3 minutes with a batch mixer set at 150° C. Thereafter, the kneaded mixture was formed into a sheet having a thickness of 50 μm by means of a two-roll mill set at 190° C., thereby producing a vinyl-chloride-based resin sheet. The vinyl-chloride-based resin sheets were evaluated for antiviral property and processability.

<Formation Conditions 102>

Each of the mixtures of Examples and Comparative Examples shown in Tables 102 and 104 was kneaded for 3 minutes with a batch mixer set at 150° C. Thereafter, the kneaded mixture was formed into a sheet having a thickness of 200 μm by means of a two-roll mill set at 180° C., thereby producing a vinyl-chloride-based resin sheet. The vinyl-chloride-based resin sheets were evaluated for antiviral property and processability.

<Antiviral Property>

As a test virus, use was made of avian influenza virus A/whistling swan/Shimane/499/83 (H5N3) strain (hereinafter referred to as H5N3 strain).

The virus was multiplied in the chorioallantoic cavity of an embryonic egg and diluted with a sterilized phosphate-buffered saline (PBS; pH, 7.2) so as to result in a concentration of $1.0 \times 10^6$ $EID_{50}/0.1$ mL. Thus, a virus-containing test liquid was prepared.

Each of the vinyl-chloride-based resin sheets having a size of 5 cm×5 cm and produced in the Examples and Comparative Examples shown in Tables 101 to 104 was placed on a petri dish. A 0.22-mL portion of the virus-containing test liquid was placed on the surface of the vinyl-chloride-based resin sheet, and this sheet was covered with a polyethylene film of 4 cm×4 cm. This petri dish was lidded and allowed to stand still for 1 hour in an incubator set at 20° C. After the 1 hour, the virus-containing liquid on the surface of each vinyl-chloride-based resin sheet was collected and diluted tenfold in stages. The diluted virus-containing liquid was inoculated in an amount of 0.1 mL with a syringe into the chorioallantoic cavity of an embryonic egg aged 10 days.

After the inoculation, the embryonic egg was incubated at 37° C. for 2 days, and whether or not the virus had multiplied within the chorioallantoic cavity was determined by a hemagglutination test. The virus titer ($\log_{10}EID_{50}/0.1$ mL) was calculated by the Reed & Muench method.

As a blank, the virus-containing test liquid before the test (i.e., the virus-containing test liquid which had not been brought into contact with the vinyl-chloride-based resin sheet) was examined to calculate the virus titer ($\log_{10}EID_{50}/0.1$ mL) in the procedure described above. The antiviral properties of each vinyl-chloride-based resin sheet was evaluated in terms of the difference obtained by subtracting the virus titer of the virus-containing liquid which had undergone 1-hour contact with the vinyl-chloride-based resin sheet from the virus titer of the virus-containing liquid before the test. The larger the difference is, the higher the antiviral properties of the vinyl-chloride-based resin sheet is.

A: the difference between the virus titer (before test) and the virus titer (after 1 hour) is 4 or larger B: the difference between the virus titer (before test) and the virus titer (after 1 hour) is 3 or larger but less than 4

C: the difference between the virus titer (before test) and the virus titer (after 1 hour) is 2 or larger but less than 3

D: the difference between the virus titer (before test) and the virus titer (after 1 hour) is less than 2

<Processability/Sheet Formation>

Each composition was evaluated for roll processability during the formation of a vinyl-chloride-based resin sheet with the two-roll mill.

A: satisfactory
B: processable without arousing problem
C: processable although the processability is slightly poor
D: unable to be processed <Processability/Plate-out>

Each composition was evaluated for plate-out on the roll surfaces during the formation of a vinyl-chloride-based resin sheet with the two-roll mill.

A: no plate-out
B: plate-out occurred slightly
C: plate-out occurred
D: plate-out occurred on the whole roll surfaces <Processability/Initial Discoloration>

Each vinyl-chloride-based resin sheet formed with the two-roll mill was evaluated for initial discoloration in terms of yellowness.

Using "SM Color Computer", manufactured by Suga Test Instruments Co., Ltd., the yellowness of the vinyl-chloride-based resin sheet was determined in accordance with JIS K 7373 (2006). The yellowness of the reference sample, in which (suspension vinyl-chloride-based resin):(vinyl-chloride-based resin for paste)=100:0 and which contained no sodium dodecylbenzenesulfonate, was used as a reference to evaluate the difference between the reference yellowness and the yellowness of the vinyl-chloride-based resin sheet in accordance with the following criteria.

Difference in yellowness=(yellowness of vinyl-chloride-based resin sheet)−(yellowness of reference sample)

A: the difference in yellowness is less than +1.0
B: the difference in yellowness is +1.0 or larger but less than +2.0

C: the difference in yellowness is +2.0 or larger but less than +3.0
D: the difference in yellowness is +3.0 or larger <Processability, Overall Evaluation>

The processability of each composition during the sheet formation therefrom with the two-roll mill was evaluated while taking account of all of the sheet formation, plate-out, and initial discoloration.

A: satisfactory
B: processable without arousing problem
C: processable although the processability is slightly poor
D: unable to be processed Examples 101 to 107

Mixtures obtained by mixing a suspension vinyl-chloride-based resin with a vinyl-chloride-based resin for paste which contained 5.0% by weight sodium dodecylbenzenesulfonate, as shown in Table 101, were formed by the method described under <Formation Conditions 101> above, thereby producing antiviral vinyl-chloride-based resin sheets for interior decoration in which the contents of the sulfonic-acid-based surfactant were 0.5-4.2 parts by weight. The antiviral properties and the processability were evaluated.

Examples 108 and 109

Mixtures obtained by mixing a suspension vinyl-chloride-based resin with a vinyl-chloride-based resin for paste which contained no sodium dodecylbenzenesulfonate and adding thereto sodium dodecylbenzenesulfonate so as to result in a content of the sulfonic-acid-based surfactant of 2.0 parts by weight were formed by the method described under <Formation Conditions 101> above, thereby producing antiviral vinyl-chloride-based resin sheets for interior decoration. The antiviral sheets were evaluated. Incidentally, the Examples shown in Table 101 are rigid antiviral vinyl-chloride-based resin sheets to which no plasticizer has been added.

Examples 110 to 114, 117, and 118

Mixtures obtained by mixing a suspension vinyl-chloride-based resin with a vinyl-chloride-based resin for paste which contained 5.0% by weight sodium dodecylbenzenesulfonate, as shown in Table 102, were formed by the method described under <Formation Conditions 102> above, thereby producing antiviral vinyl-chloride-based resin sheets for interior decoration in which the contents of the sulfonic-acid-based surfactant were 1.0-4.2 parts by weight. The antiviral sheets were evaluated.

Examples 115 and 116

Mixtures obtained by mixing a suspension vinyl-chloride-based resin with a vinyl-chloride-based resin for paste which contained 7.5% by weight sodium dodecylbenzenesulfonate, as shown in Table 102, were formed by the method described under <Formation Conditions 102> above, thereby producing antiviral vinyl-chloride-based resin sheets for interior decoration in which the contents of the sulfonic-acid-based surfactant were 1.0-2.1 parts by weight. The antiviral sheets were evaluated. Incidentally, the Examples shown in Table 102 are flexible antiviral vinyl-chloride-based resin sheets to which a plasticizer has been added.

Comparative Examples 101 to 104

Antiviral vinyl-chloride-based resin sheets for interior decoration in which the contents of a sulfonic-acid-based surfactant were 0-0.25 parts by weight and 5.0-5.3 parts by weight, as shown in Table 103, were produced by the method described under <Formation Conditions 101> above. The antiviral properties and the processability were evaluated. Incidentally, the Comparative Examples shown in Table 103 are rigid antiviral vinyl-chloride-based resin sheets to which no plasticizer has been added.

Comparative Examples 105 to 108

Antiviral vinyl-chloride-based resin sheets for interior decoration in which the contents of a sulfonic-acid-based surfactant were 0-0.25 parts by weight and 5.0-5.3 parts by weight, as shown in Table 104, were produced by the method described under <Formation Conditions 102> above. The antiviral sheets were evaluated. Incidentally, the Comparative Examples shown in Table 104 are flexible antiviral vinyl-chloride-based resin sheets to which a plasticizer has been added.

TABLE 101

| | | | | Example | | | | | | | | |
|---|---|---|---|---|---|---|---|---|---|---|---|---|
| | | | Unit | 101 | 102 | 103 | 104 | 105 | 106 | 107 | 108 | 109 |
| Recipe | Poly(vinyl chloride) | 10A-1 | parts | 0 | 0 | 0 | 0 | 0 | 0 | 0 | 0 | 0 |
| | | 10A-2 | parts | 90 | 80 | 70 | 60 | 50 | 40 | 20 | 60 | 50 |
| | Poly(vinyl chloride) | 10B-1 | parts | 10 | 20 | 30 | 40 | 50 | 60 | 80 | 0 | 0 |
| | | 10B-2 | parts | 0 | 0 | 0 | 0 | 0 | 0 | 0 | 0 | 0 |
| | | 10B-3 | parts | 0 | 0 | 0 | 0 | 0 | 0 | 0 | 40 | 50 |
| | Plasticizer | 10C-1 | parts | 0 | 0 | 0 | 0 | 0 | 0 | 0 | 0 | 0 |
| | Stabilizer | 10D-1 | parts | 3 | 3 | 3 | 3 | 3 | 3 | 3 | 3 | 3 |
| | Additive | 10E-1 | parts | 0 | 0 | 0 | 0 | 0 | 0 | 0 | 2 | 2 |
| Composition | Suspension poly(vinyl chloride)-based resin | | parts | 90 | 81 | 71 | 61 | 51 | 41 | 21 | 60 | 50 |
| | Poly(vinyl chloride)-based resin for paste | | parts | 10 | 19 | 29 | 39 | 49 | 59 | 79 | 40 | 50 |
| | Content of sulfonic-acid-based surfactant | | parts | 0.5 | 1.0 | 1.5 | 2.0 | 2.6 | 3.1 | 4.2 | 2.0 | 2.0 |
| | Content of plasticizer | | parts | 0 | 0 | 0 | 0 | 0 | 0 | 0 | 0 | 0 |
| Test results | Antiviral property | | | C | C | B | B | A | A | A | B | B |
| | Processability | Sheet formation | | A | A | A | B | B | C | C | C | C |
| | | Plate-out | | A | A | B | B | C | C | C | C | C |
| | | Initial discoloration | | A | A | B | B | B | C | C | B | C |
| | | Overall evaluation of processability | | A | A | A | B | B | C | C | C | C |

TABLE 102

| | | | | Example | | | | | | | | |
|---|---|---|---|---|---|---|---|---|---|---|---|---|
| | | | Unit | 110 | 111 | 112 | 113 | 114 | 115 | 116 | 117 | 118 |
| Recipe | Poly(vinyl chloride) | 10A-1 | parts | 80 | 70 | 60 | 40 | 20 | 87 | 73 | 60 | 40 |
| | | 10A-2 | parts | 0 | 0 | 0 | 0 | 0 | 0 | 0 | 0 | 0 |
| | Poly(vinyl chloride) | 10B-1 | parts | 20 | 30 | 40 | 60 | 80 | 0 | 0 | 40 | 60 |
| | | 10B-2 | parts | 0 | 0 | 0 | 0 | 0 | 13 | 27 | 0 | 0 |
| | | 10B-3 | parts | 0 | 0 | 0 | 0 | 0 | 0 | 0 | 0 | 0 |
| | Plasticizer | 10C-1 | parts | 30 | 30 | 30 | 30 | 30 | 30 | 30 | 25 | 25 |
| | Stabilizer | 10D-1 | parts | 3 | 3 | 3 | 3 | 3 | 3 | 3 | 3 | 3 |
| | Additive | 10E-1 | parts | 0 | 0 | 0 | 0 | 0 | 0 | 0 | 0 | 0 |
| Composition | Suspension poly(vinyl chloride)-based resin | | parts | 81 | 71 | 61 | 41 | 21 | 88 | 75 | 61 | 41 |
| | Poly(vinyl chloride)-based resin for paste | | parts | 19 | 29 | 39 | 59 | 79 | 12 | 25 | 39 | 59 |
| | Content of sulfonic-acid-based surfactant | | parts | 1.0 | 1.5 | 2.0 | 3.1 | 4.2 | 1.0 | 2.1 | 2.0 | 3.1 |
| | Content of plasticizer | | parts | 30 | 30 | 31 | 31 | 31 | 30 | 31 | 26 | 26 |
| Test results | Antiviral property | | | C | B | A | A | A | C | A | A | A |
| | Processability | Sheet formation | | A | B | B | C | C | B | B | B | C |
| | | Plate-out | | A | B | C | C | C | B | C | C | C |
| | | Initial discoloration | | A | A | B | C | C | A | B | B | C |
| | | Overall evaluation of processability | | A | B | B | C | C | B | B | B | C |

TABLE 103

|  |  |  | Unit | Comparative Example | | | |
|---|---|---|---|---|---|---|---|
|  |  |  |  | 101 | 102 | 103 | 104 |
| Recipe | Poly(vinyl chloride) | 10A-1 | parts | 0 | 0 | 0 | 0 |
|  |  | 10A-2 | parts | 100 | 95 | 5 | 0 |
|  | Poly(vinyl chloride) | 10B-1 | parts | 0 | 5 | 95 | 100 |
|  |  | 10B-2 | parts | 0 | 0 | 0 | 0 |
|  |  | 10B-3 | parts | 0 | 0 | 0 | 0 |
|  | Plasticizer | 10C-1 | parts | 0 | 0 | 0 | 0 |
|  | Stabilizer | 10D-1 | parts | 3 | 3 | 3 | 3 |
|  | Additive | 10E-1 | parts | 0 | 0 | 0 | 0 |
| Composition | Suspension poly(vinyl chloride)-based resin |  | parts | 100 | 95 | 5 | 0 |
|  | Poly(vinyl chloride)-based resin for paste |  | parts | 0 | 5 | 95 | 100 |
|  | Content of sulfonic-acid-based surfactant |  | parts | 0 | 0.25 | 5.0 | 5.3 |
|  | Content of plasticizer |  | parts | 0 | 0 | 0 | 0 |
| Test results | Antiviral property |  |  | D | D | N.D. | N.D. |
|  | Processability | Sheet formation |  | A | A | D | D |
|  |  | Plate-out |  | A | A | D | D |
|  |  | Initial discoloration |  | A | A | D | N.D. |
|  |  | Overall evaluation of processability |  | A | A | D | D |

TABLE 104

|  |  |  | Unit | Comparative Example | | | |
|---|---|---|---|---|---|---|---|
|  |  |  |  | 105 | 106 | 107 | 108 |
| Recipe | Poly(vinyl chloride) | 10A-1 | parts | 100 | 95 | 5 | 0 |
|  |  | 10A-2 | parts | 0 | 0 | 0 | 0 |
|  | Poly(vinyl chloride) | 10B-1 | parts | 0 | 5 | 95 | 100 |
|  |  | 10B-2 | parts | 0 | 0 | 0 | 0 |
|  |  | 10B-3 | parts | 0 | 0 | 0 | 0 |
|  | Plasticizer | 10C-1 | parts | 30 | 30 | 30 | 30 |
|  | Stabilizer | 10D-1 | parts | 3 | 3 | 3 | 3 |
|  | Additive | 10E-1 | parts | 0 | 0 | 0 | 0 |
| Makeup | Suspension poly(vinyl chloride)-based resin |  | parts | 100 | 95 | 5 | 0 |
|  | Poly(vinyl chloride)-based resin for paste |  | parts | 0 | 5 | 95 | 100 |
|  | Content of sulfonic-acid-based surfactant |  | parts | 0 | 0.25 | 5.0 | 5.3 |
|  | Content of plasticizer |  | parts | 30 | 30 | 31 | 32 |
| Test results | Antiviral property |  |  | D | D | A | N.D. |
|  | Processability | Sheet formation |  | A | A | C | D |
|  |  | Plate-out |  | A | A | D | D |
|  |  | Initial discoloration |  | A | A | C | N.D. |
|  |  | Overall evaluation of processability |  | A | A | D | D |

In the rigid antiviral vinyl-chloride-based resin sheets shown in Table 101, effective antiviral properties are obtained when the content of the sulfonic-acid-based surfactant is 0.5 parts by weight or higher (Example 101 and Comparative Example 102). More desirable antiviral properties are obtained when the content thereof is 1.5 parts by weight or higher, and even more desirable antiviral properties are obtained when the content thereof is 2.5 parts by weight or higher (Examples 103 and 105).

Meanwhile, the composition in which the proportion of the vinyl-chloride-based resin for paste exceeds 90 parts by weight and the proportion of the suspension vinyl-chloride-based resin is less than 10 parts by weight, per 100 parts by weight of the poly(vinyl chloride)-based resin, cannot be formed into a sheet (Comparative Example 103).

In the flexible antiviral vinyl-chloride-based resin sheets shown in Table 102, there is a tendency similar to that of the rigid antiviral vinyl-chloride-based resin sheets. Namely, high antiviral properties are obtained when the content of the sulfonic-acid-based surfactant is 2.0 parts by weight or higher (Example 112). Furthermore, as in the case of the rigid antiviral vinyl-chloride-based resin sheets, the composition in which the proportion of the vinyl-chloride-based resin for paste exceeds 90 parts by weight and the proportion of the suspension vinyl-chloride-based resin is less than 10 parts by weight cannot be formed into a sheet (Comparative Example 107).

A comparison in antiviral property between rigid antiviral vinyl-chloride-based resin sheets (Table 101) and flexible antiviral vinyl-chloride-based resin sheets (Table 102) shows that when the content of the sulfonic-acid-based surfactant is 2.0 parts by weight, the flexible antiviral vinyl-chloride-based resin sheet (Example 112) has higher antiviral properties than the rigid antiviral vinyl-chloride-based resin sheet (Example 104). Consequently, flexible antiviral vinyl-chloride-based resin sheets are more apt to produce an antiviral effect.

In Table 101, compositions which are equal in the content of a sulfonic-acid-based surfactant are compared. Specifically, a comparison between Example 104, in which a PVC (poly(vinyl chloride)) resin into which a sulfonic-acid-based surfactant had been incorporated beforehand was used, and Example 108, in which a sulfonic-acid-based surfactant was added during sheet formation, shows that the two sheets are equal in antiviral property. However, the Example in which a sulfonic-acid-based surfactant had been incorporated beforehand into the vinyl-chloride-based resin for paste was superior in the evaluation of sheet formation and plate-out. Consequently, use of a vinyl-chloride-based resin for paste into which a sulfonic-acid-based surfactant has been incorporated beforehand brings about better processability. As described above, use of a vinyl-chloride-based resin for paste to which a sulfonic-acid-based surfactant was added during production of the vinyl-chloride-based resin for paste brings about excellent processability and excellent antiviral properties.

Examples 108 and 109 are Examples in which a vinyl-chloride-based resin for paste to which no sulfonic-acid-based surfactant had been added during production thereof was mixed with a suspension vinyl-chloride-based resin in different ratios. In these Examples, a sulfonic-acid-based surfactant was added during sheet formation. A comparison between Examples 108 and 109 shows that the antiviral properties do not depend on the proportion of the suspension vinyl-chloride-based resin. However, the comparison shows that the Example in which the proportion of the suspension vinyl-chloride-based resin is higher has a smaller difference in yellowness and hence better unsusceptibility to initial discoloration.

[Second Aspect]

The compounding agents used in the Examples and the Comparative Examples are the following substances.

Poly(vinyl chloride)-based resin 20A-1: suspension poly(vinyl chloride)-based resin; average degree of polymerization, 1,000

Poly(vinyl chloride)-based resin 20B-1: poly(vinyl chloride)-based resin for paste; average degree of polymerization, 850 (content of sodium dodecylbenzenesulfonate, 5.0 wt %)

Poly(vinyl chloride)-based resin 20B-2: poly(vinyl chloride)-based resin for paste; average degree of polymerization, 850 (content of sodium dodecylbenzenesulfonate, 10.0 wt %)

Sulfonic-acid-based surfactant 20C-1: sodium alkylbenzenesulfonate; purity, 90% (trade name, NANSA (registered trademark) HS90/S, manufactured by Huntsman Japan K.K.)

Plasticizer 20D-1: di-2-ethylhexyl phthalate

Stabilizer 20E-1: Ba-Zn-based metal soap

Stabilizer 20E-2: Ba-Zn-based metal soap

Stabilizer 20E-3: epoxidized soybean oil

Viscosity-lowering agent 20E-1: fatty-acid-ester-based surfactant

Filler 20G-1: lightweight calcium carbonate (treated with fatty acid); specific-surface-area diameter, 1.5 p.m (calculated from BET specific surface area)

<Formation Conditions 201>

Each of the mixtures of the Examples shown in Table 201 and the Comparative Examples shown in Table 202 was kneaded for 3 minutes with a batch mixer set at 150° C. Thereafter, the kneaded mixture was formed into a sheet having a thickness of 350 μm by means of a two-roll mill set to a temperature of 180° C., thereby producing an interior decorative sheet.

<Formation Conditions 202>

The mixture of Comparative Example 206 shown in Table 202 was mixed and defoamed under vacuum to produce a vinyl-chloride-based sol composition. This vinyl-chloride-based sol composition was applied with a bar coater to a fabric-backed flexible PVC (poly(vinyl chloride)) sheet as a base to thereby form a resin layer on the base. Next, the sol composition applied was dried in a 205° C. oven for 5 minutes to solidify the resin layer, thereby producing an interior decorative sheet.

<Antiviral Property>

A virus-containing test liquid was prepared in the same manner as in [First Aspect], and the virus titer was calculated. The antiviral properties were evaluated in accordance with the following.

A: the difference between the virus titer (before test) and the virus titer (after 1 hour) is 4 or larger B: the difference between the virus titer (before test) and the virus titer (after 1 hour) is 2 or larger but less than 4

C: the difference between the virus titer (before test) and the virus titer (after 1 hour) is less than 2

<Handleability>

The mixtures of Examples and Comparative Examples shown in Table 201 and Table 202 each were evaluated for handleability during the mixing thereof (Evaluation Criteria)

A: no particular problem.

B: the mixture becomes sol with the lapse of time but arouses no problem concerning handling.

C: the mixture is prone to become sol and has poor handleability.

<Processability>

Each mixture was evaluated for roll processability during the formation of an interior decorative sheet therefrom with the two-roll mill.

(Evaluation Criteria)

A: the mixture can be processed without arousing problem.

B: the mixture becomes prone to stick to the rolls, but the processing is possible.

C: the mixture sticks to the rolls and the processing is impossible.

<Coloring Due to Processing>

Coloring due to processing was evaluated by visually examining the yellowness of each of the interior decorative poly(vinyl chloride) resin sheets produced in the Examples and Comparative Examples shown in Table 201 and Table 202.

(Evaluation Criteria)

A: no yellowness.

B: slight yellowness is seen but is not problematic in practical use.

C: yellowness is noticeable to considerably affect the appearance.

<Water Blushing>

Each of the interior decorative sheets having a size of 10 cm×10 cm and produced in the Examples and Comparative Examples shown in Table 201 and Table 202 was placed on a petri dish. A sponge having a size of 3 cm×3 cm×3 cm and impregnated with distilled water was placed on the surface of the interior decorative poly(vinyl chloride) resin sheet. This petri dish was lidded and allowed to stand still in an environment of 20° C. and 65% RH for 24 hours. Thereafter, the sponge and the water were removed, and the interior decorative sheet was allowed to stand still for 24 hours and then visually evaluated for blushing.

(Evaluation Criteria)

A: the sheet has not blushed or has blushed to an unnoticeable degree.

B: the sheet has blushed slightly but the blushing is not problematic in practical use.

C: blushing is noticeable to considerably affect the appearance.

TABLE 201

|  |  | Unit | Example 201 | 202 | 203 | 204 | 205 | 206 | 207 |
|---|---|---|---|---|---|---|---|---|---|
| Recipe | Suspension poly(vinyl chloride) | 20A-1 parts | 60 | 60 | 10 | 85 | 60 | 40 | 60 |
|  | Poly(vinyl chloride) for paste | 20B-1 parts | 42.1 | 42.1 |  | 15.8 |  | 63.2 | 42.1 |
|  |  | 20B-2 parts |  |  | 100 |  | 44.4 |  |  |
|  | Sulfonic-acid-based surfactant | 20C-1 parts |  |  |  |  |  |  |  |
|  | Plasticizer | 20D-1 parts | 35 | 50 | 10 | 90 | 32 | 70 | 50 |
|  | Stabilizer | 20E-1 parts | 3 | 3 | 3 | 3 | 3 | 3 | 3 |
|  |  | 20E-2 parts |  |  |  |  |  |  |  |
|  |  | 20E-3 parts | 4 | 4 | 4 | 4 | 4 | 4 | 4 |
|  | Viscosity-lowering agent | 20F-1 parts |  |  |  |  |  |  |  |
|  | Filler | 20G-1 parts |  |  |  |  |  |  | 30 |
| Makeup | Suspension poly(vinyl chloride)-based resin |  | parts | 60 | 60 | 10 | 85 | 60 | 40 | 60 |
|  | Poly(vinyl chloride)-based resin for paste | parts | 40 | 40 | 90 | 15 | 40 | 60 | 40 |
|  | Poly(vinyl chloride)-based resin | parts | 100 | 100 | 100 | 100 | 100 | 100 | 100 |
|  | Sulfuric-acid-based surfactant | parts | 2.1 | 2.1 | 10.0 | 0.8 | 4.4 | 3.2 | 2.1 |
|  | Plasticizer | parts | 35 | 50 | 10 | 90 | 32 | 70 | 50 |
| Test results | Antiviral property |  | B | A | A | B | A | A | A |
|  | Handleability |  | A | B | A | B | A | B | A |
|  | Roll processability |  | A | A | B | B | A | A | A |
|  | Coloring due to processing |  | A | A | B | A | A | B | A |
|  | Blushing |  | A | A | B | A | A | B | A |
| Formation method |  |  | rolling | rolling | rolling | rolling | rolling | rolling | rolling |

TABLE 202

|  |  | Unit | Comparative Example 201 | 202 | 203 | 204 | 205 | 206 |
|---|---|---|---|---|---|---|---|---|
| Recipe | Suspension poly(vinyl chloride) | 20A-1 parts | 100 |  | 100 | 60 | 60 |  |
|  | Poly(vinyl chloride) for paste | 20B-1 parts |  | 105.3 |  | 42.1 | 42.1 | 105.3 |
|  |  | 20B-2 parts |  |  |  |  |  |  |
|  | Sulfonic-acid-based surfactant | 20C-1 parts |  |  |  | 2.2 |  |  |
|  | Plasticizer | 20D-1 parts | 35 | 35 | 35 | 5 | 120 | 35 |
|  | Stabilizer | 20E-1 parts | 3 | 3 | 3 | 3 | 3 |  |
|  |  | 20E-2 parts |  |  |  |  |  | 3 |
|  |  | 20E-3 parts | 4 | 4 | 4 | 4 | 4 |  |
|  | Viscosity-lowering agent | 20F-1 parts |  |  |  |  |  | 7 |
|  | Filler | 20G-1 parts |  |  |  |  |  |  |
| Composition | Suspension poly(vinyl chloride)-based resin | parts | 100 | 0 | 100 | 60 | 60 | 0 |
|  | Poly(vinyl chloride)-based resin for paste | parts | 0 | 100 | 0 | 40 | 40 | 100 |
|  | Poly(vinyl chloride)-based resin | parts | 100 | 100 | 100 | 100 | 100 | 100 |
|  | Sulfuric-acid-based surfactant | parts | 0 | 5.3 | 2.0 | 2.1 | 2.1 | 5.3 |
|  | Plasticizer | parts | 35 | 35 | 35 | 5 | 120 | 35 |

TABLE 202-continued

|  |  | Unit | Comparative Example | | | | | |
|---|---|---|---|---|---|---|---|---|
|  |  |  | 201 | 202 | 203 | 204 | 205 | 206 |
| Test results | Antiviral property |  | C | A | B | B | A | A |
|  | Handleability |  | A | C | A | A | C | — |
|  | Roll processability |  | A | A | A | C | C | — |
|  | Coloring due to processing |  | A | B | C | C | A | A |
|  | Blushing |  | A | B | A | A | B | C |
| Formation method |  |  | rolling | rolling | rolling | rolling | rolling | paste application |

It can be seen from a comparison between Examples 201 to 206, which are shown in Table 201, and Comparative Example 201, which is shown in Table 202, that the inclusion of a sulfonic-acid-based surfactant has imparted antiviral properties. From a comparison between Example 201 and Example 202, it can be seen that in cases when the addition amount of the sulfonic-acid-based surfactant is the same, the antiviral properties are enhanced by increasing the addition amount of the plasticizer.

A comparison between Example 201 and Comparative Example 202 shows that by blending a poly(vinyl chloride)-based resin for paste with a suspension poly(vinyl chloride)-based resin in a proportion within the range according to the invention, excellent handleability is obtained in cases when the addition amount of the plasticizer is the same.

It can be seen from a comparison between Example 201 and Comparative Example 203 that excellent unsusceptibility to coloring due to processing is obtained by using a poly(vinyl chloride)-based resin for paste to which a sulfonic-acid-based surfactant has been added beforehand, without using a method in which the sulfonic-acid-based surfactant is directly added.

A comparison between Example 201 and Comparative Examples 204 and 205 shows that the composition is rendered excellent in terms of handleability, roll processability, and unsusceptibility to coloring due to processing, by regulating the addition amount of the plasticizer so as to be in the range according to the invention.

It can be seen from a comparison between Example 201 and Comparative Example 206 that excellent resistance to water blushing is obtained by performing not paste application but roll processing which is a melt forming technique.

It can be seen from Example 202 and Comparative Example 207 that handleability is improved by adding a filler.

Meanwhile, interior decorative sheets to each of which a back layer had been laminated were produced, although not shown in the tables. The back layer was obtained in the following manner.

A hundred parts by weight of suspension poly(vinyl chloride) resin 20A-1 was kneaded together with 55 parts by weight of plasticizer 20D-1, 200 parts by weight of filler 20G-1, 3 parts by weight of stabilizer 20E-1, and 4 parts by weight of stabilizer 20E-3 for 3 minutes by means of a batch mixer set at 150° C. Thereafter, the kneaded mixture was formed into a sheet having a thickness of about 1.65 mm by means of a two-roll mill set at 180° C. The back layer thus obtained was thermally laminated to each of the surface layers of Examples 201 to 207, thereby obtaining interior decorative sheets for flooring material, each of which was composed of the surface layer and the back layer laminated thereto. These interior decorative sheets for flooring material each had a thickness of about 2 mm. These interior decorative sheets for flooring material were tested, and gave results which were similar to those shown in Table 201.

[Third Aspect]

The compounding agents used in the Examples and the Comparative Examples are the following substances.

Poly(vinyl chloride) 30A-1: poly(vinyl chloride)-based resin for paste; average degree of polymerization, 4,500 (sodium dodecylbenzenesulfonate, 10.0 wt %)

Poly(vinyl chloride) 30A-2: poly(vinyl chloride)-based resin for paste; average degree of polymerization, 4,500 (sodium dodecylbenzenesulfonate, 1.0 wt %)

Poly(vinyl chloride) 30A-3: poly(vinyl chloride)-based resin for paste; average degree of polymerization, 850 (sodium dodecylbenzenesulfonate, 5.0 wt %)

Poly(vinyl chloride) 30a-1: poly(vinyl chloride)-based resin for paste; average degree of polymerization, 4,500

Sulfonic-acid-based surfactant 40B-1: sodium alkylbenzenesulfonate; purity, 90%; (trade name, NANSA (registered trademark) HS90/S, manufactured by Huntsman Japan K.K.)

Plasticizer 30C-1: di-2-ethylhexyl phthalate

Stabilizer 30D-1: Ba-Zn-based metal soap

Stabilizer 30D-2: epoxidized soybean oil

Viscosity-lowering agent 30E-1: fatty-acid-ester-based surfactant

Each of the mixtures of Examples and Comparative Examples shown in Table 301 was mixed and defoamed under vacuum to produce a poly(vinyl chloride)-based sol composition. This poly(vinyl chloride)-based sol composition was applied with a bar coater to a fabric-backed flexible PVC (poly(vinyl chloride)) sheet as a base to thereby form a poly(vinyl chloride)-based resin layer on the base. Next, the sol composition applied was dried in a 205° C. oven for 5 minutes to solidify the poly(vinyl chloride)-based resin layer, thereby obtaining an interior decorative poly(vinyl chloride)-based resin sheet.

<Defoamability>

A 40-g portion of each of the poly(vinyl chloride)-based sol compositions obtained through mixing in the Examples and Comparative Examples shown in Table 301 was placed in a 1-L cup and defoamed under vacuum. In this operation, the foam height which was the maximum height of the elevated sol surface level and the foam breaking period which was the period required for the sol to come to generate no foam were measured, and the defoamability was evaluated in terms of the foam height and the foam breaking period. For the evaluation, Comparative Example 301 was used as a reference.

A: both the foam height and the foam breaking period are substantially the same as in Comparative Example 301.

B: the foam height is slightly larger and the foam breaking period is somewhat longer than in Comparative Example 301.

C: the foam height is far larger and the foam breaking period is longer than in Comparative Example 301.
<Applicability>
The poly(vinyl chloride)-based sol compositions produced in the Examples and Comparative Examples shown in Table 301 were each applied to a base with a bar coater, and the applicability thereof during this application was evaluated.

A: the sol composition can be applied without arousing any problem.

B: slight unevenness in application is seen but is not problematic in practical use.

C: the sol composition is difficult to apply with bar coater.
<Appearance>
The appearance of each of the interior decorative poly (vinyl chloride)-based resin sheets produced in the Examples and Comparative Examples shown in Table 301 was evaluated.

A: the appearance is satisfactory.

B: slight unevenness in application is seen but is not problematic in practical use.

C: there are considerable unevenness in application and many residual cells, resulting in poor appearance.
<Antiviral Property>
A virus-containing test liquid was prepared in the same manner as in [First Aspect], and the virus titer was calculated. The antiviral properties were evaluated in accordance with the following.

A: the difference between the virus titer (before test) and the virus titer (after 1 hour) is 4 or larger B: the difference between the virus titer (before test) and the virus titer (after 1 hour) is 2 or larger but less than 4

C: the difference between the virus titer (before test) and the virus titer (after 1 hour) is less than 2
<Antifouling Property>
Six standard rubber blocks were introduced into a Snell capsule tester described in JIS K 3920 (2009), and each sheet was set therein so that the surface layer came into contact with the rubber blocks. This tester was subjected to 5 cycles of rotation, each cycle being composed of 5-minute normal rotation and 5-minute reverse rotation each at a rotation speed of 50 rpm. Thereafter, the sheet was taken out and the degree of adhesion of a heel mark was examined to evaluate the fouling. Furthermore, the fouled surface was wiped with a dry cloth, and the cleanability was evaluated in terms of the degree of the residual adhesion of the heel mark. The antifouling properties were evaluated in terms of both the fouling and the cleanability.

Fouling

A: substantially no adhesion (only slight adhesion is observed)

B: adhesion occurred

C: considerable adhesion occurred

Cleanability

A: fouling substances are removable (after cleaning, the fouling is not noticeable)

B: fouling substances are partly difficult to remove (after cleaning, noticeable fouling remains)

C: fouling substances are mostly difficult to remove
<Blushing>
Each of the interior decorative poly(vinyl chloride)-based resin sheets having a size of 10 cm×10 cm and produced in the Examples and Comparative Examples shown in Table 301 was placed on a petri dish. A sponge having a size of 3 cm×3 cm×3 cm and impregnated with distilled water was placed on the surface of the interior decorative poly(vinyl chloride)-based sheet. This petri dish was lidded and allowed to stand still in an environment of 20° C. and 65% RH for 24 hours. Thereafter, the sponge and the water were removed, and the interior decorative sheet was allowed to stand still for 24 hours and then examined for ΔE* using "SM Color Computer", manufactured by Suga Test Instruments Co., Ltd. The larger the value of ΔE* is, the severer the blushing is.

TABLE 301

| | | | | Example | | | | | | |
|---|---|---|---|---|---|---|---|---|---|---|
| | | | Unit | 301 | 302 | 303 | 304 | 305 | 306 |
| Recipe | Poly(vinyl | 30A-1 | parts | 5 | 20 | | | 65 | 30 |
| | chloride) | 30A-2 | parts | | | 100 | | | |
| | | 30A-3 | parts | | | | 100 | | |
| | | 30a-1 | parts | 95 | 80 | | | 35 | 70 |
| | Sulfonic-acid-based surfactant | 30B-1 | parts | | | | | | |
| | Plasticizer | 30C-1 | parts | 36 | 30 | 20 | 12 | 65 | 80 |
| | Stabilizer | 30D-1 | parts | 3 | 3 | 3 | 3 | 3 | 3 |
| | | 30D-2 | parts | 3 | 3 | 3 | 3 | 3 | 3 |
| | Viscosity-lowering agent | 30E-1 | parts | 7 | 10 | 15 | 20 | 5 | 3 |
| Composition | Poly(vinyl chloride)-based resin for paste | | parts | 100 | 100 | 100 | 100 | 100 | 100 |
| | Sulfonic-acid-based surfactant | | parts | 0.5 | 2.0 | 1.0 | 5.3 | 7.0 | 3.1 |
| | Plasticizer | | parts | 36 | 31 | 20 | 13 | 70 | 82 |
| Test results | Defoamability | | | A | A | A | B | B | A |
| | Applicability | | | A | A | A | B | A | A |
| | Appearance | | | A | A | A | B | B | B |
| | Antiviral property | | | B | A | A | A | A | A |
| | Antifouling property | Fouling | | A | A | A | A | B | B |
| | | Cleanability | | A | A | A | A | B | B |
| | ΔE* (blushing) | | | 1.6 | 3 | 1.7 | 5.5 | | 3.5 |

TABLE 301-continued

|  |  |  |  | Comparative Example | | | | |
|---|---|---|---|---|---|---|---|---|
|  |  |  | Unit | 301 | 302 | 303 | 304 | 305 |
| Recipe | Poly(vinyl chloride) | 30A-1 | parts |  | 100 |  | 20 |  |
|  |  | 30A-2 | parts |  |  |  |  |  |
|  |  | 30A-3 | parts |  |  | 100 |  |  |
|  |  | 30a-1 | parts | 100 |  |  | 80 | 100 |
|  | Sulfonic-acid-based surfactant | 30B-1 | parts |  |  |  |  | 2 |
|  | Plasticizer | 30C-1 | parts | 36 | 32 | 8 | 120 | 36 |
|  | Stabilizer | 30D-1 | parts | 3 | 3 | 3 | 3 | 3 |
|  |  | 30D-2 | parts | 3 | 3 | 3 | 3 | 3 |
|  | Viscosity-lowering agent | 30E-1 | parts | 7 | 10 | 20 | 5 | 7 |
| Composition | Poly(vinyl chloride)-based resin for paste |  | parts | 100 | 100 | 100 | 100 | 100 |
|  | Sulfonic-acid-based surfactant |  | parts | 0.0 | 11.1 | 5.3 | 2.0 | 1.8 |
|  | Plasticizer |  | parts | 36 | 36 | 8 | 122 | 36 |
| Test results | Defoamability |  |  | A | C | B | B | A |
|  | Applicability |  |  | A | B | C | B | C |
|  | Appearance |  |  | A | C | C | C | C |
|  | Antiviral property |  |  | C | A | A | A | B |
|  | Antifouling property | Fouling |  | A | C | A | C | A |
|  |  | Cleanability |  | A | C | A | C | B |
|  | ΔE* (blushing) |  |  | 1.2 |  | 5.6 | 3 |  |

It can be seen from a comparison between Examples 301 to 305 and Comparative Example 301 that the inclusion of a sulfonic-acid-based surfactant has imparted antiviral properties.

From a comparison between Example 302 and Comparative Example 302, it can be seen that excellent properties in terms of defoamability, appearance, and antifouling property are obtained by regulating the content of the sulfonic-acid-based surfactant so as to be within the range according to the invention.

A comparison between Examples 304 to 306 and Comparative Examples 303 and 304 shows that excellent paste applicability and an excellent appearance are obtained by regulating the addition amount of the plasticizer so as to be within the range according to the invention.

It can be seen from a comparison between Example 303 and Comparative Example 305 that excellent properties in terms of applicability, appearance, and antiviral property are obtained by using a poly(vinyl chloride)-based resin for paste into which a sulfonic-acid-based surfactant has been incorporated beforehand.

Furthermore, it can be seen that the lower the content of the sulfonic-acid-based surfactant, the less the blushing.

[Fourth Aspect]

The compounding agents used in the Examples and the Comparative Examples are the following substances.

Vinyl-chloride-based resin 40A-1: suspension vinyl-chloride-based resin; average degree of polymerization, 1,000

Vinyl-chloride-based resin 40A-2: suspension vinyl-chloride-based resin; average degree of polymerization, 1,300

Vinyl-chloride-based resin 40A-3: vinyl-chloride-based resin for paste; average degree of polymerization, 850 (content of sodium dodecylbenzenesulfonate, 3.0 wt %)

Vinyl-chloride-based resin 40A-4: vinyl-chloride-based resin for paste; average degree of polymerization, 850 (content of sodium dodecylbenzenesulfonate, 5.0 wt %)

Vinyl-chloride-based resin 40A-5: vinyl-chloride-based resin for paste; average degree of polymerization, 850 (content of sodium dodecylbenzenesulfonate, 7.5 wt %)

Sulfonic-acid-based surfactant 40B-1: sodium alkylbenzenesulfonate; purity, 90%

Plasticizer 40C-1: di-2-ethylhexyl phthalate

Silicone-based copolymer 40D-1: silicone/acrylic graft copolymer (acrylic resin chains have been disposed as side chains of silicone) silicone content, 70%

Silicone-based copolymer 40D-2: graft copolymer based on silicone/acrylic composite rubber Filler 40E-1: lightweight calcium carbonate (treated with fatty acid); specific-surface-area diameter, 1.5 p.m (calculated from BET specific surface area)

Processing aid 40E-1: acrylic polymeric processing aid

Stabilizer 40G-1: Ba-Zn-based metal soap

Coloring inhibitor 40H-1: sodium perchlorate

Each of the mixtures of Examples and Comparative Examples shown in Tables 401 to 404 was kneaded for 5 minutes with a batch mixer set at 150° C. Thereafter, the kneaded mixture was formed into a sheet having a thickness of 0.35 mm by means of a two-roll mill set at 180° C. and subsequently laminated to a back layer constituted of a flexible vinyl-chloride-based sheet having a thickness of 1.7 mm, thereby producing an interior decorative sheet. The interior decorative sheets were each evaluated for antiviral property, antifouling property, and processability. Furthermore, the yellowness of the surface layer was measured.

In each of the Examples shown in Table 405, the mixture of Example 405 was kneaded for 5 minutes with a batch mixer set at 150° C., thereafter formed into a sheet having a thickness of 0.35 mm by means of a two-roll mill set at 180° C., and then laminated to a back layer constituted of a flexible vinyl-chloride-based sheet having a thickness of 1.7 mm, thereby producing an interior decorative sheet. Finally, the interior decorative sheet was embossed with a press forming machine to form fine recesses and protrusions in the surface. The surface roughness of the surface layer in which the fine recesses and protrusions had been formed was determined by the method described above. These interior decorative sheets were evaluated for antiviral property and antifouling property.

<Antiviral Property>

A virus-containing test liquid was prepared in the same manner as in [First Aspect], and the virus titer was calculated. The antiviral properties were evaluated in accordance with the following.

A: the difference between the virus titer (before test) and the virus titer (after 1 hour) is 4 or larger B: the difference between the virus titer (before test) and the virus titer (after 1 hour) is 3 or larger but less than 4

C: the difference between the virus titer (before test) and the virus titer (after 1 hour) is 2 or larger but less than 3

D: the difference between the virus titer (before test) and the virus titer (after 1 hour) is less than 2

<Antifouling Property>

Six standard rubber blocks were introduced into a Snell capsule tester described in JIS K 3920 (2009), and each sheet was set therein so that the surface layer came into contact with the rubber blocks. This tester was subjected to 5 cycles of rotation, each cycle being composed of 5-minute normal rotation and 5-minute reverse rotation each at a rotation speed of 50 rpm. Thereafter, the sheet was taken out and the degree of adhesion of a heel mark was examined to evaluate the fouling. Furthermore, the fouled surface was wiped with a dry cloth, and the cleanability was evaluated in terms of the degree of the residual adhesion of the heel mark. The antifouling properties were evaluated in terms of both the fouling and the cleanability.

Fouling
A: substantially no adhesion (only slight adhesion is observed)
B: adhesion occurred
C: considerable adhesion occurred Cleanability
A: fouling substances are removable (after cleaning, the fouling is not noticeable)
B: fouling substances are partly difficult to remove (after cleaning, noticeable fouling remains)
C: fouling substances are mostly difficult to remove <Processability>

Each composition was evaluated for roll processability during the sheet formation therefrom with the two-roll mill at 180° C.
A: satisfactory
B: processable without arousing problem
C: processable although the processability is slightly poor
D: unable to be processed <Yellowness>

The yellowness was determined using "SM Color Computer", manufactured by Suga Test Instruments Co., Ltd., in accordance with JIS K 7373 (2006).

<Surface Roughness of Surface Layer>

The surface roughness of the surface layer was determined using "Surface Roughness/Shape Analyzer" manufactured by Tokyo Seimitsu Co., Ltd., in accordance with JIS B 0601 (2001).

TABLE 401

|  |  |  | Unit | Example 401 | 402 | 403 | 404 | 405 | 406 | 407 | 408 |
|---|---|---|---|---|---|---|---|---|---|---|---|
| Recipe | Vinyl-chloride-based resin | 40A-1 | parts | 100 | 100 | 100 | 100 | 100 | 66 | 34 | |
| | | 40A-2 | parts | | | | | | | | |
| | | 40A-3 | parts | | | | | | 34 | 66 | 100 |
| | | 40A-4 | parts | | | | | | | | |
| | | 40A-5 | parts | | | | | | | | |
| | Sulfonic-acid-based surfactant | 40B-1 | parts | 2.3 | 3.5 | 3.5 | 3.5 | 5.9 | | | |
| | Plasticizer | 40C-1 | parts | 32 | 32 | 32 | 32 | 32 | 32 | 32 | 32 |
| | Silicone-based copolymer | 40D-1 | parts | 3 | 5 | 10 | 10 | | 10 | 10 | 10 |
| | | 40D-2 | parts | | | | | 10 | | | |
| | Filler | 40E-1 | parts | | | | 10 | 30 | | | |
| | Processing aid | 40E-1 | parts | 4 | 4 | 4 | 4 | 4 | 4 | 4 | 4 |
| | Stabilizer | 40G-1 | parts | 3 | 3 | 3 | 3 | 3 | 3 | 3 | 3 |
| | Coloring inhibitor | 40H-1 | parts | | | | | | | | |
| Composition | Suspension poly(vinyl chloride)-based resin | | parts | 100 | 100 | 100 | 100 | 100 | 67 | 35 | 0 |
| | Poly(vinyl chloride)-based resin for paste | | parts | 0 | 0 | 0 | 0 | 0 | 33 | 65 | 100 |
| | Content of sulfonic-acid-based surfactant | | parts | 2.1 | 3.2 | 3.2 | 3.2 | 5.3 | 1.0 | 2.0 | 3.1 |
| | Content of plasticizer | | parts | 32 | 32 | 32 | 32 | 32 | 32 | 33 | 33 |
| | Content of silicone-based copolymer | | parts | 3 | 5 | 10 | 10 | 10 | 10 | 10 | 10 |
| Test results | Antiviral property | | | C | B | B | B | A | C | B | A |
| | Antifouling property | Fouling | | B | B | A | B | B | A | A | A |
| | | Cleanability | | A | A | A | A | B | A | A | A |
| | Processability | | | B | C | C | B | C | B | C | C |
| | Yellowness | | | 10 | 27 | 27 | 27 | 54 | 3 | 4 | 10 |

TABLE 402

|  |  |  | Unit | Example 409 | 410 | 411 | 412 | 413 | 414 | 415 | 416 |
|---|---|---|---|---|---|---|---|---|---|---|---|
| Recipe | Vinyl-chloride-based resin | 40A-1 | parts | 80 | 60 | 40 | 60 | 60 | 60 | 60 | 60 |
| | | 40A-2 | parts | | | | | | | | |
| | | 40A-3 | parts | | | | | | | | |
| | | 40A-4 | parts | 20 | 40 | 60 | 40 | 40 | 40 | 40 | 40 |
| | | 40A-5 | parts | | | | | | | | |

TABLE 402-continued

|  |  |  | Unit | Example 409 | 410 | 411 | 412 | 413 | 414 | 415 | 416 |
|---|---|---|---|---|---|---|---|---|---|---|---|
| Composition | Sulfonic-acid-based surfactant | 40B-1 | parts |  |  |  |  |  |  |  |  |
|  | Plasticizer | 40C-1 | parts | 32 | 32 | 32 | 32 | 32 | 14 | 40 | 32 |
|  | Silicone-based copolymer | 40D-1 | parts | 5 | 5 | 5 | 5 | 10 | 5 | 5 | 10 |
|  |  | 40D-2 | parts |  |  |  |  |  |  |  |  |
|  | Filler | 40E-1 | parts |  |  |  |  |  |  |  | 10 |
|  | Processing aid | 40F-1 | parts | 4 | 4 | 4 |  | 4 | 4 | 3 | 4 |
|  | Stabilizer | 40G-1 | parts | 3 | 3 | 3 | 3 | 3 | 3 | 3 | 3 |
|  | Coloring inhibitor | 40H-1 | parts |  |  |  |  |  |  |  |  |
|  | Suspension poly(vinyl chloride)-based resin |  | parts | 81 | 61 | 41 | 61 | 61 | 61 | 61 | 61 |
|  | Poly(vinyl chloride)-based resin for paste |  | parts | 19 | 39 | 59 | 39 | 39 | 39 | 39 | 39 |
|  | Content of sulfonic-acid-based surfactant |  | parts | 1.0 | 2.0 | 3.1 | 2.0 | 2.0 | 2.0 | 2.0 | 2.0 |
|  | Content of plasticizer |  | parts | 32 | 33 | 33 | 33 | 33 | 14 | 41 | 33 |
|  | Content of silicone-based copolymer |  | parts | 5 | 5 | 5 | 5 | 10 | 5 | 5 | 10 |
| Test results | Antiviral property |  |  | C | B | A | B | B | C | B | B |
|  | Antifouling property | Fouling |  | A | A | B | A | A | A | B | A |
|  |  | Cleanability |  | A | A | A | A | A | A | B | A |
|  | Processability |  |  | A | A | C | C | C | C | A | A |
|  | Yellowness |  |  | 3 | 4 | 6 | 4 | 5 | 9 | 3 | 4 |

TABLE 403

|  |  |  | Unit | Example 417 | 418 | 419 | 420 | 421 | 422 | 423 | 424 |
|---|---|---|---|---|---|---|---|---|---|---|---|
| Recipe | Vinyl-chloride-based resin | 40A-1 | parts | 73 | 60 | 73 |  | 50 |  |  |  |
|  |  | 40A-2 | parts |  |  |  |  |  | 50 | 50 | 50 |
|  |  | 40A-3 | parts |  |  |  |  |  |  |  |  |
|  |  | 40A-4 | parts |  |  |  |  | 50 | 50 | 50 | 50 |
|  |  | 40A-5 | parts | 27 | 40 | 27 | 100 |  |  |  |  |
|  | Sulfonic-acid-based surfactant | 40B-1 | parts |  |  |  |  |  |  |  |  |
|  | Plasticizer | 40C-1 | parts | 29 | 29 | 40 | 30 | 32 | 32 | 32 | 32 |
|  | Silicone-based copolymer | 40D-1 | parts | 5 | 5 | 10 | 20 | 10 | 10 | 10 | 10 |
|  |  | 40D-2 | parts |  |  |  |  |  |  |  |  |
|  | Filler | 40E-1 | parts |  |  | 30 | 5 | 10 | 10 | 20 | 20 |
|  | Processing aid | 40F-1 | parts | 4 | 4 | 4 | 4 | 4 | 4 | 4 | 4 |
|  | Stabilizer | 40G-1 | parts | 3 | 3 | 3 | 3 | 3 | 3 | 3 | 3 |
|  | Coloring inhibitor | 40H-1 | parts |  |  |  |  |  |  |  | 0.2 |
| Composition | Suspension poly(vinyl chloride)-based resin |  | parts | 75 | 62 | 75 | 0 | 51 | 51 | 51 | 51 |
|  | Poly(vinyl chloride)-based resin for paste |  | parts | 25 | 38 | 25 | 100 | 49 | 49 | 49 | 49 |
|  | Content of sulfonic-acid-based surfactant |  | parts | 2.1 | 3.1 | 2.1 | 8.1 | 2.6 | 2.6 | 2.6 | 2.6 |
|  | Content of plasticizer |  | parts | 30 | 30 | 41 | 32 | 33 | 33 | 33 | 33 |
|  | Content of silicone-based copolymer |  | parts | 5 | 5 | 10 | 22 | 10 | 10 | 10 | 10 |
| Test results | Antiviral property |  |  | B | A | A | A | A | A | A | A |
|  | Antifouling property | Fouling |  | A | B | B | B | A | A | A | B |
|  |  | Cleanability |  | A | A | B | A | B | A | A | B |
|  | Processability |  |  | B | B | B | C | C | C | B | B |
|  | Yellowness |  |  | 5 | 7 | 6 | 13 | 6 | 6 | 5 | 4 |

TABLE 404

|  |  |  | Unit | Comparative Example | | | | | |
|---|---|---|---|---|---|---|---|---|---|
|  |  |  |  | 401 | 402 | 403 | 404 | 405 | 406 |
| Recipe | Vinyl-chloride-based resin | 40A-1 | parts | 100 | 60 | 60 | 60 | 60 | 100 |
|  |  | 40A-2 | parts |  |  |  |  |  |  |
|  |  | 40A-3 | parts |  | 40 | 40 | 40 | 40 |  |
|  |  | 40A-4 | parts |  |  |  |  |  |  |
|  |  | 40A-5 | parts |  |  |  |  |  |  |
|  | Sulfonic-acid-based surfactant | 40B-1 | parts |  |  |  |  |  | 12 |
|  | Plasticizer | 40C-1 | parts | 32 | 4 | 54 | 54 | 34 | 40 |
|  | Silicone-based copolymer | 40D-1 | parts | 3 | 10 |  | 20 | 5 | 5 |
|  |  | 40D-2 | parts |  |  |  |  |  |  |
|  | Filler | 40E-1 | parts |  |  |  |  | 100 |  |
|  | Processing aid | 40E-1 | parts | 3 | 4 |  | 5 | 5 | 3 |
|  | Stabilizer | 40G-1 | parts | 3 | 3 | 3 | 3 | 3 | 3 |
|  | Coloring inhibitor | 40H-1 | parts |  |  |  |  |  |  |
| Composition | Suspension poly(vinyl chloride)-based resin |  | parts | 100 | 61 | 61 | 61 | 61 | 100 |
|  | Poly(vinyl chloride)-based resin for paste |  | parts | 0 | 39 | 39 | 39 | 39 | 0 |
|  | Content of sulfonic-acid-based surfactant |  | parts | 0 | 1.2 | 1.2 | 1.2 | 1.2 | 10.8 |
|  | Content of plasticizer |  | parts | 32 | 4 | 55 | 55 | 34 | 40 |
|  | Content of silicone-based copolymer |  | parts | 3 | 10 | 0 | 20 | 5 | 5 |
| Test results | Antiviral property |  |  | D | — | B | B | B | — |
|  | Antifouling property |  | Fouling | B | — | C | B | C | — |
|  |  |  | Cleanability | A | — | C | C | C | — |
|  | Processability |  |  | B | D | C | C | C | D |
|  | Yellowness |  |  |  | 2 | 5 | 4 | 4 |  |

TABLE 405

|  | Example | | | |
|---|---|---|---|---|
|  | 425 | 426 | 427 | 428 |
| Shape of grain | flat | sharp | broad | broad |
| Arithmetic average roughness of surface layer Ra (μm) | 0.3 | 1.5 | 5.5 | 12.5 |
| Antiviral property | B | B | A | A |
| Antifouling property Fouling | A | B | B | A |
| Cleanability | A | B | B | A |

As apparent from Tables 401 to 404, it can be seen that the addition of a sulfonic-acid-based surfactant has imparted antiviral properties and the addition of a silicone-based copolymer has improved the antifouling properties. Furthermore, from a comparison between Example 421 and Example 422, it can be seen that Example 422, in which the suspension vinyl-chloride-based resin has a higher degree of polymerization, is more effective in diminishing the decrease in antifouling property due to the increase in the content of the sulfonic-acid-based surfactant. A comparison between Example 402 and Example 411 shows that the sheet produced using a vinyl-chloride-based resin for paste which contained a sulfonic-acid-based surfactant not only has a lower yellowness, i.e., has undergone less coloring, but also exhibits higher antiviral properties. A comparison between Example 413 and Example 416 shows that the addition of a filler has enhanced processability.

Table 405 shows that an improvement in antiviral property was attained by changing the shape of the surface.

[Fifth Aspect]

The following materials were used in the Examples and the Comparative Examples.

Vinyl chloride resin α for paste (containing 5.0 wt % DBS)
Vinyl chloride resin β for paste (containing 2.5 wt % DBS)
Vinyl chloride resin γ for paste (containing 1.0 wt % DBS)
Vinyl chloride resin δ for paste (containing 10 wt % DBS)
DOP (plasticizer)
Ba—Zn-based stabilizer
ADCA (foaming agent)
Calcium carbonate (filler)
DBS (undiluted powder form)

In Example 501, vinyl chloride resin α for paste, into which 5.0% by weight sodium dodecylbenzenesulfonate (DBS) had been incorporated beforehand as a sulfonic-acid-based surfactant, was mixed with vinyl chloride resin γ for paste, into which 1.0% by weight DBS had been incorporated beforehand, a plasticizer (DOP), a stabilizer, a foaming agent (ADCA), a filler (calcium carbonate), a diluent, and a pigment in the respective amounts shown in Table 501, thereby producing a paste sol. This paste sol was applied to backing paper as a base layer with a paste coater to thereby form a resin layer on the base layer. Thus, a wallpaper base was obtained. Thereafter, this wallpaper base was subjected to mechanical embossing while being foamed at 210° C. Thus, a specimen was obtained.

Details of Examples 502 to 509 and Comparative Examples 501 and 502 are as shown in Table 501. These specimens were produced in accordance with the method used in Example 501. In Examples 505 and 506, a topcoat layer was formed with a gravure printing machine after gelation, and this sheet was subjected to drying at 120° C. and then to mechanical embossing.

[Evaluation of Wallpaper Appearance]

The appearance of each wallpaper obtained was visually evaluated.

A: the surface has no surface defects and retains beautiful appearance.

B: there is surface ruggedness, although it is on a permissible level.

C: there are noticeable surface defects, e.g., streaks.

[Evaluation of Antiviral Property]

A virus-containing test liquid was prepared in the same manner as in [First Aspect], and the virus titer was calculated.

The difference between "virus titer (after 1 hour)" and "virus titer (before test)" indicates the degree of antiviral properties. The larger the difference, the higher the antiviral properties.

Third grade: a break in the surface layer is clearly observed.

Second grade: a break in the surface occurred and the backing material, e.g., paper, is clearly seen therethrough (length, less than 1 cm).

First grade: a break in the surface occurred and the backing material, e.g., paper, is clearly seen therethrough (length, 1 cm or larger).

TABLE 501

|  |  | Example | | | | | | | | | Comparative Example | |
|---|---|---|---|---|---|---|---|---|---|---|---|---|
|  |  | 501 | 502 | 503 | 504 | 505 | 506 | 507 | 508 | 509 | 501 | 502 |
| Vinyl chloride α for paste (DBS, 5.0 wt %) | | 5 | 25 | | 25 | 25 | 50 | 25 | 100 | | | |
| Vinyl chloride β for paste (DBS, 2.5 wt %) | | | | 100 | | | | | | | | |
| Vinyl chloride γ for paste (DBS, 1.0 wt %) | | 95 | 75 | | 75 | 75 | 50 | 75 | | | 100 | 100 |
| Vinyl chloride δ for paste (DBS, 10 wt %) | | | | | | | | | | 100 | | |
| DOP (plasticizer) | | 60 | 60 | 60 | 60 | 60 | 60 | 60 | 60 | 60 | 60 | 60 |
| Ba—Zn-based stabilizer | | 2.5 | 2.5 | 2.5 | 2.5 | 2.5 | 2.5 | 2.5 | 2.5 | 2.5 | 2.5 | 2.5 |
| ADCA (foaming agent) | | 2.5 | 2.5 | 2.5 | 5 | 2.5 | 2.5 | 0 | 2.5 | 2.5 | 2.5 | 2.5 |
| Calcium carbonate (filler) | | 100 | 100 | 100 | 100 | 100 | 100 | 100 | 100 | 100 | 100 | 100 |
| Diluent | | 9 | 9 | 9 | 9 | 9 | 9 | 9 | 9 | 9 | 9 | 9 |
| Pigment | | 25 | 25 | 25 | 25 | 25 | 25 | 25 | 25 | 25 | 25 | 25 |
| DBS (undiluted) | | | | | | | | | | | | 1.5 |
| Topcoat | | — | — | — | — | present | present | — | — | — | — | — |
| Content of DBS based on vinyl chloride resin, wt % | | 1.2 | 2.0 | 2.5 | 2.0 | 2.0 | 3.0 | 2.0 | 5.0 | 10.0 | 1.0 | 2.5 |
| Wallpaper appearance | | A | A | A | B | A | A | A | A | A | A | C |
| Index to antiviral property (virus titer: $\log_{10}\text{EID}_{50}/0.1$ mL) | before virus test | 6.3 | 6.3 | 6.3 | 6.3 | 6.0 | 6.3 | 6.3 | 6.3 | 6.3 | 6.3 | 6.3 |
| | after 1-hour contact with virus | 2.3 | <0.5 | <0.5 | <0.5 | 1.8 | <0.8 | <0.5 | <0.5 | <0.5 | 3.8 | <0.5 |
| Surface strength | | third grade | third grade | third grade | first grade | fourth grade | fourth grade | third grade | third grade | third grade | third grade | first grade |

[Evaluation of Surface Strength]

The surface strength was evaluated through a test according to a regulation for the performance of surface-reinforced wallpapers (prescribed in the year 2004; revised in the year 2009; edition 3-2) prescribed by Japan Wallcoverings Association. Three test pieces having a size of 30 mm×250 mm were cut out of each specimen and used. As the main body of a testing device was used a rubbing tester type II provided for in JIS L0849. As a rubber was used a claw and holder prescribed for in the regulation for the performance of surface-reinforced wallpapers. The load on the rubber was 1.96 N, and the material of the claw used was SUS402-J2. The tip of the claw had dimensions of 4.0 mm (width)×2.0 mm (thickness), and the edges of the tip had R dimensions of 0.10 mm for the start side and 0.15 mm for the return side. Each test piece was fixed to the test piece table of the tester so that the test piece was parallel with the reciprocating direction of the rubber. The rubber was placed on the test piece and reciprocated five times over a traveling distance of 120 mm at a frequency of 30 reciprocations per minute. Thereafter, the test piece was detached from the test piece table and visually examined for the degree of surface scratches. The results were compared with the following criteria. Specimens in the fourth or higher grade are deemed to have surface strength.

Fifth grade: at a glance, especially no change is observed.

Fourth grade: surface scratches are slightly observed, but no relatively large break or the like was observed in the surface layer.

[Evaluation Results]

Examples 501 to 506 reduced the virus titer form the value for "before contact with virus" to the value for "after 1-hour contact with virus" by at least 4.0 (i.e., to about $10^{-4.0} = 1/10,000$). These Examples have high antiviral properties while retaining a beautiful appearance.

Furthermore, Examples 505 and 506 showed that the disposition of a topcoat layer has enhanced the surface strength to the fourth or higher grade.

In contrast, Comparative Example 501 gave test results in which the virus titer had decreased from the value for "before contact with virus" to the value for "after 1-hour contact with virus" by as small as 2.5 (i.e., to $10^{-2.5}$=about 1/310) since the content of the sulfonic-acid-based surfactant was as low as 1.0% by weight based on the vinyl chloride resin. Namely, Comparative Example 501 had lower antiviral properties than the Examples. Furthermore, in Comparative Example 2, in which an undiluted powder of DBS had been added as a sulfonic-acid-based surfactant during paste production, had a poor wallpaper appearance although having improved antiviral properties.

INDUSTRIAL APPLICABILITY

According to the first aspect of the invention, since the antiviral vinyl-chloride-based resin sheet has high antiviral properties, the antiviral sheet can be used as sheets for interior decorative materials, including wallpapers, flooring materials, ceiling materials, and curtains, for dwelling houses, facilities, or the like, such as hospitals, care homes, protective institutions, schools, kindergartens, community centers, gymnasiums, railway stations, dwelling houses, and apartment buildings. The antiviral vinyl-chloride-based resin sheet can be used also as sheets for furniture including chairs, sofas, and the like. Furthermore, the antiviral vinyl-chloride-based resin sheet can be processed into the shapes of, for example, protective clothing, protective wears, protective aprons, hats or caps, gloves, fool covers, or raincoats by subjecting the sheet to secondary processing such as cutting, thermal fusion, or solvent melt bonding.

Moreover, in preparation for the occurrence of a pandemic, the antiviral vinyl-chloride-based resin sheet can be used not only as protective clothing or protective wears for storing but also as interior decorative sheets for, for example, tents for fever outpatient services, infectious diseases, or droplet infection.

According to the second aspect of the invention, it is possible to provide an interior decorative sheet which has an excellent appearance and which rapidly reduces the virus titer that have come into contact therewith and inactivates the viruses.

According to the third aspect of the invention, it is possible to provide an interior decorative sheet which retains antiviral properties and has an advantage in that fouling substances are less apt to adhere thereto and the fouling substances, if having adhered thereto, can be removed by simple cleaning. This interior decorative sheet can hence retain a beautiful appearance over a long period without requiring periodic maintenance, e.g., an antifouling treatment.

According to the fourth aspect of the invention, it is possible to provide an interior decorative sheet which has an excellent appearance and which rapidly reduces the virus titer of and inactivates viruses that have come into contact therewith.

This interior decorative sheet of the invention is hence suitable for various buildings, vehicles, etc. In particular, the interior decorative sheet is suitable for places where a large number of people gather at a time and the risk of catching a viral infection is high, such as public facilities, e.g., hospitals, offices, health centers for the elderly, and schools, and buses and trains.

According to the fifth aspect of the invention, it is possible to provide an antiviral wallpaper which has an excellent appearance and which rapidly reduces the virus titer of and inactivates viruses that have come into contact therewith.

While the invention has been described in detail and with reference to specific embodiments thereof, it will be apparent to one skilled in the art that various changes and modifications can be made therein without departing from the spirit and scope thereof.

This application is based on a Japanese patent application filed on Jul. 12, 2013 (Application No. 2013-147100), a Japanese patent application filed on Jul. 12, 2013 (Application No. 2013-147101), a Japanese patent application filed on Jul. 12, 2013 (Application No. 2013-147102), a Japanese patent application filed on Oct. 18, 2013 (Application No. 2013-217171), and a Japanese patent application filed on Oct. 18, 2013 (Application No. 2013-217421), the contents thereof being incorporated herein by reference.

The invention claimed is:

1. An antiviral vinyl-chloride resin composition comprising:
   100 parts by weight of a poly(vinyl chloride) resin obtained by mixing 20-50 parts by weight of a vinyl-chloride resin for paste with 80-50 parts by weight of a suspension vinyl-chloride resin; and
   0.5-10.0 parts by weight of a sulfonic acid surfactant, wherein the vinyl-chloride resin for paste includes polymer particles having a particle diameter of 0.02-20.0 µm and the suspension vinyl-chloride resin includes polymer particles having a particle diameter of 50-200 µm.

2. The antiviral vinyl-chloride resin composition according to claim 1,
   wherein the poly(vinyl-chloride) resin is a resin obtained by mixing the vinyl-chloride resin for paste and the sulfonic-acid surfactant with the suspension vinyl-chloride resin.

3. The antiviral vinyl-chloride resin composition according to claim 1,
   wherein the sulfonic-acid surfactant is added during production of the vinyl-chloride resin for paste.

4. An antiviral vinyl-chloride resin sheet obtained by forming the antiviral vinyl-chloride resin composition according to claim 1.

5. A process for producing an antiviral shaped object of a vinyl-chloride resin, the process comprising:
   a step in which 20-50 parts by weight of a vinyl-chloride resin for paste which includes polymer particles having a particle diameter of 0.02-20.0 µm is mixed with 80-50 parts by weight of a suspension vinyl-chloride resin which includes polymer particles having a particle diameter of 50-200 µm; and
   a step in which a poly(vinyl chloride) resin including the vinyl-chloride resin for paste and the suspension vinyl-chloride resin is melt-shaped,
   wherein the vinyl-chloride resin for paste contains a sulfonic acid surfactant, and
   the sulfonic-acid surfactant is added in an amount of 0.5-10.0 parts by weight per 100 parts by weight of the poly(vinyl chloride) resin.

6. The process for producing an antiviral shaped object of a vinyl-chloride resin according to claim 5,
   wherein the step of melt shaping is a method of forming a sheet, and
   the antiviral shaped object of a vinyl-chloride resin is an antiviral sheet of a vinyl-chloride resin.

7. An interior decorative sheet comprising a surface layer constituted by an antiviral poly(vinyl chloride) resin composition which contains: 100 parts by weight of a poly(vinyl chloride) resin containing 20-50 parts by weight of a vinyl-chloride resin for paste which includes polymer particles having a particle diameter of 0.02-20.0 µm and 80-50 parts by weight of a suspension vinyl-chloride resin which includes polymer particles having a particle diameter of 50-200 µm; 0.5-10.0 parts by weight of a sulfonic-acid surfactant; and 10-100 parts by weight of a plasticizer.

8. The interior decorative sheet according to claim 7,
   wherein the poly(vinyl chloride) resin is a mixture of the suspension vinyl-chloride resin with the vinyl-chloride resin for paste to which the sulfonic-acid surfactant is added.

9. The interior decorative sheet according to claim 7,
   wherein the sulfonic-acid surfactant is added during a production of the vinyl-chloride resin for paste.

10. A process for producing an interior decorative sheet constituted by an antiviral poly(vinyl chloride) resin composition containing 100 parts by weight of a poly(vinyl chloride) resin containing 20-50 parts by weight of a vinyl-chloride resin for paste including polymer particles having a particle diameter of 0.02-20.0 µm and 80-50 parts by weight of a suspension vinyl-chloride resin including polymer particles having a particle diameter of 50-200 μm, 0.5-10.0 parts by weight of a sulfonic-acid surfactant, and 10-100 parts by weight of a plasticizer, the process comprising:
- a step in which the vinyl-chloride resin for paste that contains the sulfonic-acid surfactant is mixed with the suspension vinyl-chloride resin to obtain the poly(vinyl chloride) resin;
- a step in which the poly(vinyl chloride) resin is mixed with the plasticizer to obtain the antiviral poly(vinyl chloride) resin composition; and
- a step in which the antiviral poly(vinyl chloride) resin composition is melt-shaped.

* * * * *